(12) United States Patent
Garg

(10) Patent No.: US 11,742,074 B2
(45) Date of Patent: Aug. 29, 2023

(54) SYSTEMS AND METHODS FOR DISPENSING MEDICATIONS BASED ON PROXIMITY TO AN ELECTRONIC MEDICATION STORAGE CABINET

(71) Applicant: CareFusion 303, Inc., San Diego, CA (US)

(72) Inventor: Honey Garg, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 202 days.

(21) Appl. No.: 17/009,699

(22) Filed: Sep. 1, 2020

(65) Prior Publication Data

US 2021/0065887 A1    Mar. 4, 2021

Related U.S. Application Data

(60) Provisional application No. 62/895,442, filed on Sep. 3, 2019.

(51) Int. Cl.
*G16H 40/20* (2018.01)
*G16H 40/67* (2018.01)
(Continued)

(52) U.S. Cl.
CPC ........... *G16H 40/20* (2018.01); *A61J 7/0084* (2013.01); *B65D 83/0445* (2013.01);
(Continued)

(58) Field of Classification Search
None
See application file for complete search history.

(56) References Cited

U.S. PATENT DOCUMENTS 8,402,514 B1 * 3/2013 Thompson .............. H04L 63/08
726/4
9,344,436 B1 * 5/2016 Sheng ................... H04W 12/08
(Continued)

FOREIGN PATENT DOCUMENTS

CA    2509787 A1    6/2004
EP    2478887 A1    7/2012

OTHER PUBLICATIONS

Colombo, Allen B. "Cabinet Locks Go High Tech", Locksmith Ledger International, Oct. 1, 2015. (Year: 2015).*
(Continued)

*Primary Examiner* — Evangeline Barr
*Assistant Examiner* — Anne-Marie K Alderson
(74) *Attorney, Agent, or Firm* — Morgan, Lewis & Bockius LLP

(57) ABSTRACT

A method includes providing, on a computing device, when a user of the device is authorized, a user interface including respective representations of first medication administration functions and second medication administration functions associated with storage of the one or more medications and, in response to determining that the computing device is within the first predetermined area, enabling the computing device to perform the one or more first medication administration functions associated with the first predetermined area to cause, responsive to a selection of a displayed representation of the one or more first medication administration functions, a respective electronic medication storage cabinet associated with the selected displayed representation to perform an operation regarding a physical storage of a medication associated with a patient of the one or more patients, and preventing the computing device from performing the one or more second medication administration functions not associated with the first predetermined area.

21 Claims, 17 Drawing Sheets

(51) Int. Cl.

| | | |
|---|---|---|
| *G16H 10/60* | (2018.01) | |
| *G16H 20/13* | (2018.01) | |
| *A61J 7/00* | (2006.01) | |
| *B65D 83/04* | (2006.01) | |
| *G06F 21/31* | (2013.01) | |
| *G06F 21/62* | (2013.01) | |
| *H04W 4/029* | (2018.01) | |
| *A47F 3/00* | (2006.01) | |
| *A47F 3/02* | (2006.01) | |
| *A47F 3/04* | (2006.01) | |
| *G06F 3/04842* | (2022.01) | |
| *G08B 21/18* | (2006.01) | |

(52) U.S. Cl.
CPC .......... *G06F 21/31* (2013.01); *G06F 21/6245* (2013.01); *G16H 10/60* (2018.01); *G16H 20/13* (2018.01); *G16H 40/67* (2018.01); *A47F 3/002* (2013.01); *A47F 3/02* (2013.01); *A47F 3/0478* (2013.01); *A61J 2205/60* (2013.01); *G06F 3/04842* (2013.01); *G08B 21/182* (2013.01); *H04W 4/029* (2018.02)

(56) References Cited

U.S. PATENT DOCUMENTS

| | | | | |
|---|---|---|---|---|
| 2010/0030667 | A1* | 2/2010 | Chudy | G06Q 10/08 705/28 |
| 2012/0179488 | A1* | 7/2012 | Tanimoto | G06Q 10/087 705/2 |
| 2013/0079924 | A1* | 3/2013 | Garda | G16H 40/63 700/242 |
| 2014/0163726 | A1* | 6/2014 | Shoenfeld | G16H 20/13 700/241 |
| 2016/0012196 | A1* | 1/2016 | Mark | G06Q 10/00 705/2 |
| 2016/0058661 | A1* | 3/2016 | Pether | A61J 7/0481 206/534 |
| 2017/0372600 | A1* | 12/2017 | Palin | H04W 4/80 |
| 2018/0018435 | A1* | 1/2018 | Marshall | G16H 40/20 |
| 2020/0286610 | A1* | 9/2020 | Wartena | G08B 21/22 |
| 2020/0397977 | A1* | 12/2020 | Keitzmann | G07C 9/00174 |

OTHER PUBLICATIONS

International Search Report and Written Opinion for Application No. PCT/US2020/049064, dated Dec. 8, 2020, 14 pages.

\* cited by examiner

Clinician Mobile Device

| My Patients | Options |
|---|---|
| B. Sm*** | (V) (Q) (D) |
| J. Do*** | (V) (Q) (D) |
| C. Ste*** | (V) (Q) (D) |
| M. Wil*** | (V) (Q) (D) |
| T. Joh*** | (V) (Q) (D) |
| L. Eve*** | (V) (Q) (D) |

FIG. 1E

SYSTEMS AND METHODS FOR DISPENSING MEDICATIONS BASED ON PROXIMITY TO AN ELECTRONIC MEDICATION STORAGE CABINET

CROSS REFERENCE TO RELATED APPLICATIONS

This application claims the benefit of U.S. Provisional Application Ser. No. 62/895,442, entitled "SYSTEMS AND METHODS FOR DISPENSING MEDICATIONS BASED ON PROXIMITY TO AN ELECTRONIC MEDICATION STORAGE CABINET," filed on Sep. 3, 2019, the entirety of each of which is incorporated herein by reference.

TECHNICAL FIELD

This application relates generally to dispensing of medication from a device, such as an electronic medication storage cabinets used in healthcare organizations.

BACKGROUND

Electronic medication storage cabinets allow healthcare facilities to store medications and grant access to the stored medications to only authorized clinicians, such as nurses and doctors. However, such electronic medication storage cabinets can be inadvertently opened by an authorized clinician, and thereby increasing the risk of theft and/or administration of wrong medications by another clinician to another patient.

SUMMARY

Accordingly, there is a need for methods and systems that can activate and/or enable one or more medication administration functions on a computing device associated with an authorized clinician based on a location of the computing device. Such methods and systems improve medical devices configured to store medications, such as electronic medication storage cabinets, by improving security of storing medications and reducing risk of diversion, theft, and/or administration of incorrect medications to patients.

In accordance with some implementations, a method includes receiving a current location of a computing device; determining, based on the current location of the computing device, whether the computing device is within a first predetermined area associated with predetermined medication administration functions that, when activated, operate one or more electronic medication storage cabinets; confirming a user of the computing device is authorized to receive information pertaining to one or more medications associated with one or more patients; providing, for display at the computing device, based on confirming the user is authorized, a graphical user interface including respective representations of one or more first medication administration functions and one or more second medication administration functions associated with storage of the one or more medications; in response to determining that the computing device is within the first predetermined area: enabling the computing device to perform the one or more first medication administration functions associated with the first predetermined area to cause, responsive to a selection of a displayed representation of the one or more first medication administration functions, a respective electronic medication storage cabinet associated with the selected displayed representation to perform an operation regarding a physical storage of a medication associated with a patient of the one or more patients; and preventing the computing device from performing the one or more second medication administration functions not associated with the first predetermined area, wherein the respective electronic medication storage cabinet is remote from the computing device. Other aspects include corresponding systems, apparatus, and computer program products for implementation of the method.

In accordance with some implementations, a system includes a memory storing instructions and one or more processors coupled with the memory and configured to execute the instructions to cause the system to receive location information of a computing device. The one or more processors are configured to execute instructions to cause the system to receive a current location of a computing device; determine, based on the current location of the computing device, whether the computing device is within a first predetermined area associated with predetermined medication administration functions that, when activated, operate one or more electronic medication storage cabinets; confirm a user of the computing device is authorized to receive information pertaining to one or more medications associated with one or more patients; provide, for display at the computing device, based on confirming the user is authorized, a graphical user interface including respective representations of one or more first medication administration functions and one or more second medication administration functions associated with storage of the one or more medications; and when the computing device is within the first predetermined area: enable the computing device to perform one or more first medication administration functions associated with the first predetermined area to cause, responsive to a selection of a displayed representation of the one or more first medication administration functions, a respective electronic medication storage cabinet associated with the selected displayed representation to perform an operation regarding a physical storage of a medication associated with a patient of the one or more patients; and prevent the computing device from performing one or more second medication administration functions not associated with the first predetermined area, wherein the respective electronic medication storage cabinet is remote from the computing device. Other aspects include corresponding systems, apparatus, and computer program products for implementation of the system.

In accordance with some implementations, an electronic medication storage cabinet includes one or more processors and memory storing one or more programs configured for execution by the one or more processors. The one or more programs include instructions for performing the operations of any of the methods described in this application. In accordance with some implementations, a non-transitory computer-readable storage medium stores instructions that, when executed by a server system, cause the server system to perform the operations of any of the methods described in this application.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIGS. 1B-1I are user interfaces displayed on a computing device of a clinician, according to illustrative implementations.

Figure 1A:
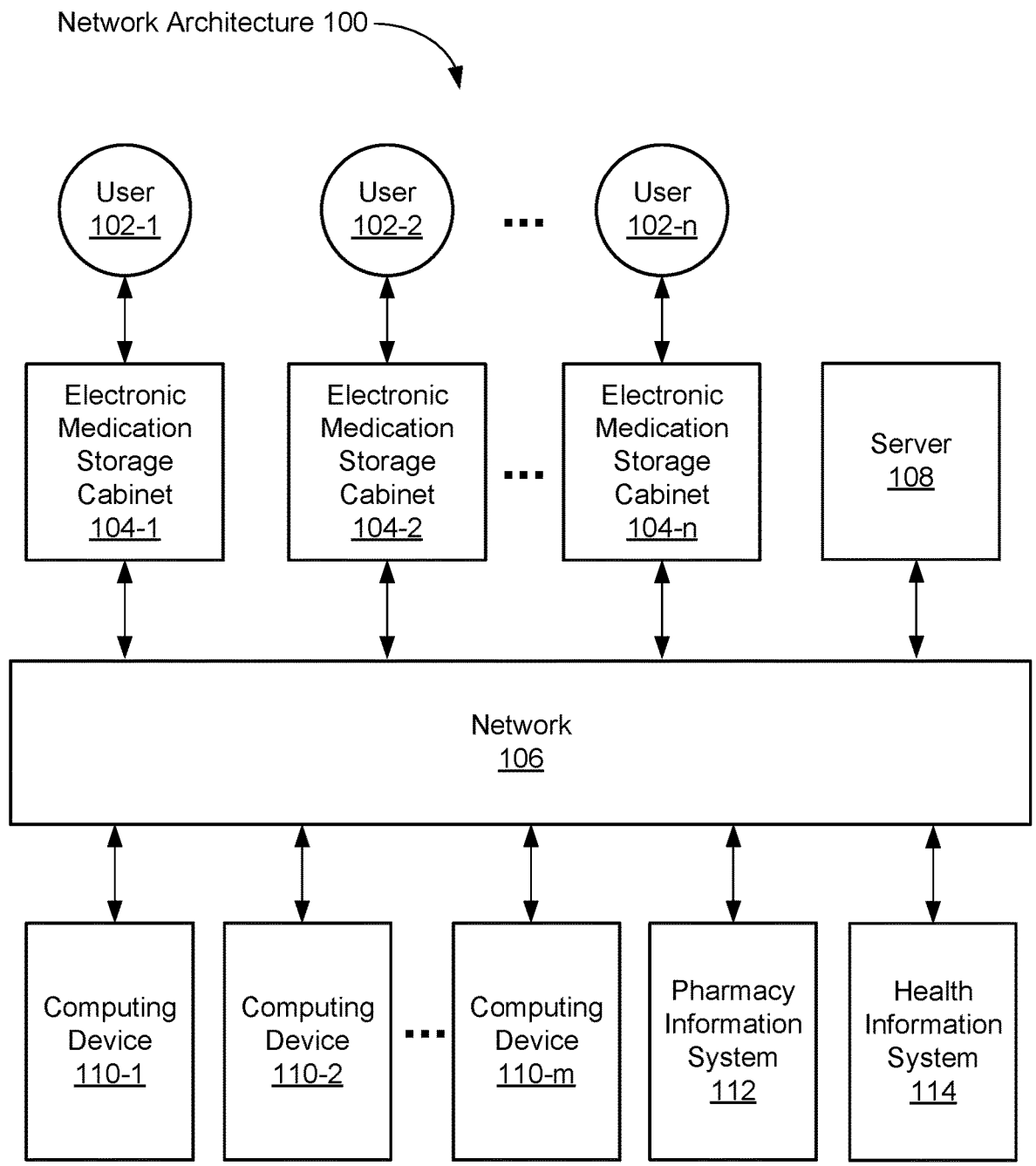
FIG. 1A is a block diagram of a network architecture for administering medication from an electronic medication storage unit, according to illustrative implementations.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various configurations of the subject disclosure and is not intended to represent the only configurations in which the subject disclosure may be practiced. The appended drawings are incorporated herein and constitute a part of the detailed description. The detailed description includes specific details for the purpose of providing a thorough understanding of the subject disclosure. However, it will be apparent to those skilled in the art that the subject disclosure may be practiced without these specific details. In some instances, structures and components are shown in block diagram form in order to avoid obscuring the concepts of the subject disclosure. Like components are labeled with identical element numbers for ease of understanding.

It will also be understood that, although the terms "first" and "second" are used herein to describe various elements, these elements should not be limited by these terms. These terms are used only to distinguish one element from another. For example, a first drawer could be termed a second drawer, and, similarly, a second drawer could be termed a first drawer, without departing from the scope of the various described implementations. The first drawer and the second drawer are both drawers, but they are not the same drawer.

The terminology used in the description of the various implementations described herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will also be understood that, although the terms "first" and "second" are used herein to describe various elements, these elements should not be limited by these terms. These terms are used only to distinguish one element from another. It will be further understood that the terms "includes," "including," "comprises," and/or "comprising" when used in the specification, specify the presence of stated features, steps, operations, elements, and/or components, but do not preclude the presence or addition of one or more other features, steps, operations, elements, components, and/or groups thereof. A clinician may include a licensed individual responsible for administration of medication at a healthcare organization. As used herein, examples of a healthcare organization include hospitals, long-term care facilities, nursing homes, out-patient treatment centers, store-front retail treatment centers, pharmacies, community clinics, non-acute care facilities, acute care facilities, and the like.

According to various aspects, the subject technology provides a means to grant and/or deny permission to a user operating a computer device (e.g., a mobile device) to perform various medication administration functions associated with a medical device remote from the user based on a location of the computing device. As an example, a medical device, such as a medication storage system, may be configured to identify whether the computing device is within a predetermined area and identify one or more functions for operating the device that are associated with the predetermined area. According to some implementations, a server associated with the medical device may identify the location of the computing device and determine whether it is within an area authorized to perform the functions. Functions may include, for example, one or more medication administration functions configured to operate, and/or selectable to operate, one or more electronic medication storage cabinets. Examples of the medication administration functions associated with different predetermined areas include, but are not limited to, viewing of ordered medications for patients in the area, queuing of ordered medications to electronic medication storage cabinets located in the area, and dispensing of ordered medications from an electronic medication storage cabinets in the area. In some implementations, a predetermined area may include an area within a threshold distance of a patient or patient room, the medical device (e.g., electronic medication storage cabinet), or area (e.g., care unit) associated with the patient or patient room, the medical device, or area. In some implementations, queuing of ordered medications function may be associated with an electronic medication storage cabinet to which the ordered medications are queued. Similarly, dispensing of ordered medications function may be associated with the electronic medication storage cabinet from which the ordered medications are queued to be dispensed.

By granting and/or denying permissions to access medication administration functionalities based on whether the computing device is within a predetermined area, the medical device and/or server is configured to allow a healthcare organization to provide and/or limit functionalities available to clinicians that, for example, may be far away from an electronic medication storage cabinet (or cabinets) storing ordered medications. For example, the clinicians may be granted the functionality to view medications and/or queue medications when far away from an electronic medication storage cabinet, but only allow the clinician to grant the functionality to dispense medications when the computing device of the clinician is very near (e.g., 3 feet) from the electronic medication storage cabinet. Additional details of granting and/or deny permissions for various functions available to the user of the computing device based on the location of the computing device are described herein with reference to FIGS. 1A-7C.

Turning now to FIG. 1A, there is shown a block diagram of a network architecture 100 in accordance with some embodiments.

As depicted in the example system architecture of FIG. 1A, a network architecture 100 may include one or more electronic medication storage cabinets 104-1, 104-2, . . . , 104-n, collectively referred to herein as electronic medication storage cabinets 104. In some implementations, an electronic medication storage cabinet 104 may be communicatively and/or operably coupled to one or more other electronically controlled and/or managed medication storage units, such as electronically controlled and/or managed medication storage towers, electronically controlled and/or managed medication storage refrigerators, and the like.

The one or more electronic medication storage cabinets 104 may be communicatively coupled to an server 108 (e.g., an electronic medication storage system server) by one or more communication networks 106. Examples of the one or more communication networks 106 include, but are not limited to, an intranet, the Internet, cellular telephone networks, mobile data networks, wide area networks, local area networks, metropolitan area networks, and the like. In some implementations, the one or more communication networks 106 include a public communication network (e.g., the Internet and/or a cellular data network), a private communications network (e.g., a private LAN or leased lines), or a combination of such communication networks.

The server 108 may be communicatively coupled to one or more computing devices 110-1, 110-2, . . . , 110-m, collectively referred to herein as computing devices 110, by one or more communication networks 106. The one or more computing devices 110 may be any computing device including, but not limited to, mobile phones, smart phones, tablet computing devices, laptops, and the like. In some implementations, the one or more computing devices 110 may include an application installed thereon that is configured to receive a clinician's access credentials (e.g., a user identifier and/or password of the clinician for that application), and provide access to one or more medication administration functions based at least on the clinician's access credentials. Each computing device 110 may include systems for determining its current location, such as a global positioning system (GPS), and configured to report its current location through the application and/or to server 108 via network 106. In some implementations, a computing device 110 may be associated with a clinician, and the association between the computing device 110 and the clinician may be stored in one or more data storage units of the server 108 and/or communicatively coupled to the server 108.

The server 108 may be communicatively coupled to a pharmacy information system 112 and/or a health information system 114, by one or more communication networks 106. The pharmacy information system 112 may be configured to receive medication orders for a patient and transmit an indication of the medication orders to the server 108. For example, based on medications prescribed to a patient, the pharmacy information system 112 may generate one or more indications of the medication orders for the patient and transmit the indications of the orders to the server 108. Additionally or in the alternative, the server 108 may transmit indications of the received medication orders to one or more clinicians assigned to the patient. Additional details are described herein with reference to FIGS. 1B-7C.

The health information system 114 may be configured to generate, maintain, update, and/or store electronic health records of one or more patients. The health information system 114 may be configured to receive data related medications prescribed to a patient, and store and/or update the medications data of a patient in a corresponding electronic health record. In some implementations, the health information system may be configured to transmit prescribed medication data to the pharmacy information system 112, and the pharmacy information system 112 may transmit one or more medication orders for the patient to the server 108.

In some implementations, the electronic medication storage cabinets 104 may be configured to transmit requests to and receive from the server 108, data related to locations of medications stored in other electronic medication storage cabinets 104. The electronic medication storage cabinets 104 may be configured to wirelessly connect (e.g., via a Bluetooth connection) to one or more computing devices 110 based on proximity of the computing devices 110. In some implementations, when connected to a computing device 110, an electronic medication storage cabinet 104 is configured to transmit a message to the server 108 indicating a successful wireless connection between the electronic medication storage cabinet 104 and the computing device 110. According to various implementations, the electronic medication storage cabinets 104 may be configured to receive instructions from the computing devices 110. For example, an electronic medication storage cabinet 104 may receive instructions to dispense one or more medications queued at the electronic medication storage cabinet 104 from the computing device 110 and, when the user of the computing device 110 is appropriately authorized, the electronic medication storage cabinet 104 may initiate a medication dispensing process for the queued medications.

In some implementations, the server 108 is a single computing device such as a computer server, while in other implementations, the server 108 is implemented by multiple computing devices working together to perform the actions of a server system (e.g., cloud computing). Additional details of the server 108 are described herein and with reference to FIG. 2.

Each of the electronic medication storage cabinets 104 may include one or more electronically controlled and/or managed movable drawers. In some implementations, some movable drawers may be of different sizes. The movable drawers may include or be configured with one or more sensor devices. For example, movable drawers may be configured with sensor devices on the inside portions of the floors of the movable drawers. In some implementations, the sensor devices may be placed in one or more patterns (e.g., grid patterns, and the like) at different locations within the movable drawers. In some implementations, the sensor devices may be placed in a grid pattern covering a major portion of the movable drawers.

Each movable drawer may have one or more pockets to store medications. In some implementations, the pockets may be different sizes and shapes. In some implementations, one or more pockets may be fixed to a particular location within the movable drawer. In some implementations, one or more pockets may be movable from a first location within the movable drawer to a second location within the movable drawer, and/or relocated to a different movable drawer within the same cabinet also configured for movable pockets, and/or removed from the movable drawer. In this regard, the storage cabinet 104 may be configured to track and/or record the location of each of the pockets so that the appropriate pocket and location can be identified when searching for a medication responsive to a request for the medication. In some implementations, one or more pockets may include a lid, and the electronic medication storage cabinet 104 may be configured to open and close the lid of the pocket. The pockets may include or be configured with transmitter devices. In some implementations, the transmitter devices of the pockets may be light based transmitter devices (e.g., laser based transmitter, and the like). In some implementations, the pockets may include radio-frequency identification (RFID) based electronic devices (e.g., RFID tags).

In some implementations, each pocket of the electronic medication storage cabinet 104 may be associated with unique identifier, and the identifier may be used to identify a location of the pocket within the electronic medication storage cabinet 104. In some implementations, a system, such as the pharmacy information system 112, may transmit information related to a pocket (e.g., an identifier of the pocket) and a medication (e.g., an identifier of the medication) to the server 108 after the medication is loaded and/or placed into the pocket of an electronic medication storage cabinet 104. In some implementations, a clinician may provide information to the server 108 identifying the medication and the pocket after the medication is stored in the pocket. For example, a clinician, after placing a medication in the pocket, may transmit an identifier of the pocket and the medication to the server 108, by providing inputs to a computing device communicatively coupled to the server 108. In some implementations, the pocket identifier may automatically be transmitted (e.g., by the cabinet) when the medication is loaded in the pocket. The server 108 may maintain and/or update a mapping between medications stored in pockets of electronic medication storage cabinets 104 and the pockets of the electronic medication storage cabinets 104 by storing received information of pockets (e.g., received identifiers of the pocket) in association with the received information of the medications (e.g., medication identifiers) stored in the pockets.

In some implementations, a computing device 110 is associated with a clinician when a clinician logs into and/or electronically signs into the disclosed application operating on the computing device 110. The application is configured to receive inputs from the clinicians and cause data related to the inputs to be transmitted to the server 108. In some implementations, the application displays one or more graphical user interfaces (GUI) and graphical items configured to receive inputs from a clinician (e.g., textboxes, radio buttons, drop down menus, and the like) and display information to the clinician (e.g., alert windows). In some implementations, the server 108 may receive location information of the computing device 110 (e.g., from the application operating on the computing device 110). Examples of location information include, but are not limited to, wireless access point information, internet protocol address, geospatial coordinates, data from a global positioning system (GPS) sensors of computing devices 110, and the like.

The server 108 may be configured to enable and/or disable medication administration functions for clinicians based on locations of the computing devices 110 associated with the clinicians. As described above, the one or more medication administration functions may be configured to operate and/or selectable to operate one or more electronic medication storage cabinets. Examples of medication administration functions include but are not limited to viewing a pending ordered medication for a patient, viewing details of the pending ordered medication, queuing the ordered medication to an electronic mediation storage cabinet 104, dispensing the ordered medication from an electronic medication storage cabinet 104, and the like. In some implementations, a healthcare organization may specify a set of rules and/or configuration data indicating certain areas outside of the healthcare organization, certain areas surrounding the healthcare care organization, areas within the healthcare organization, and/or areas near and/or proximal to electronic medication storage cabinets 104 as threshold areas, and the server 108 may enable and/or disable one or more medication administration functions.

Figure 1B:
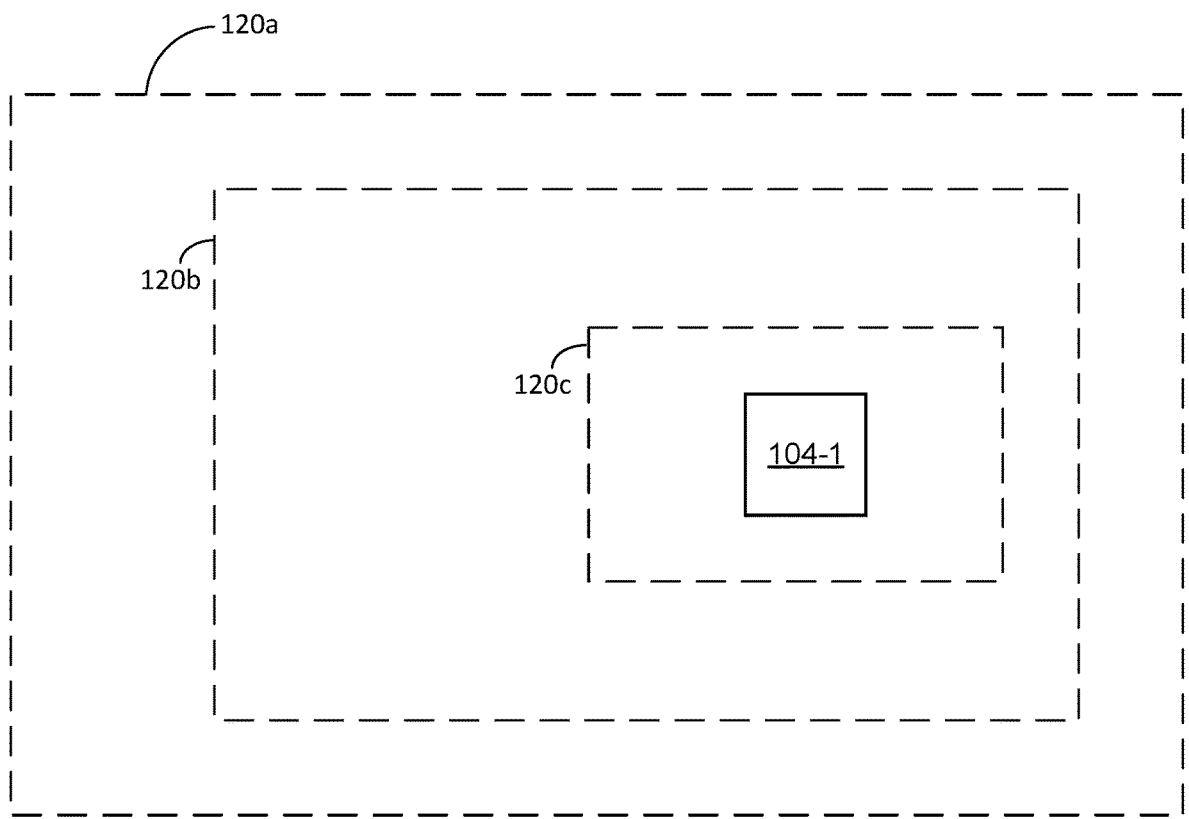

For example, as shown in FIG. 1B, a healthcare organization may specify three threshold areas. Area 120a may cover an area that is very near to the healthcare organization, such as a parking lot adjacent to the healthcare organization's building, area 120b may cover areas that are inside the healthcare organization's building, such as lobby and/or one or floors of the healthcare organization, and area 120c may cover area within a threshold distance of an electronic medication storage cabinet 104-1, such as 3 to 10 feet from the electronic medication storage cabinet 104. The depicted areas 120a, 120b, 120c are depicted as overlapping for illustrative purposes and, in some implementations, one or more of areas 120a, 120b, 120c may not overlap or other non-overlapping areas may also be implemented. For example, area 120c may be a subset of and overlap area 120b, while area 120a may be independent and not overlap areas 120b and 120c.

The server 108 may stored a set of rules that specify the medication administration function(s) available for different threshold areas predetermined by the healthcare organization and, based on the stored rules and location information of the computing devices 110, may be configured to enable and/or disable medication administration functions. For example, if the stored set of rules indicate that all medication administration functions should be disabled if the computing device 110 is outside of threshold area 120a, and the server 108 determines that a computing device 110 is outside of the threshold area 120, then the server 108 may disable all medication administration functions by disabling permissions for those functions for the computing device 110 and transmit the updated permissions to the computing device 110. In some implementations, the server 108 may transmit an instruction to computing device 110 to cause the application executed on the computing device 110 to disable user interfaces associated with the medication administration functions.

Figure 1C:
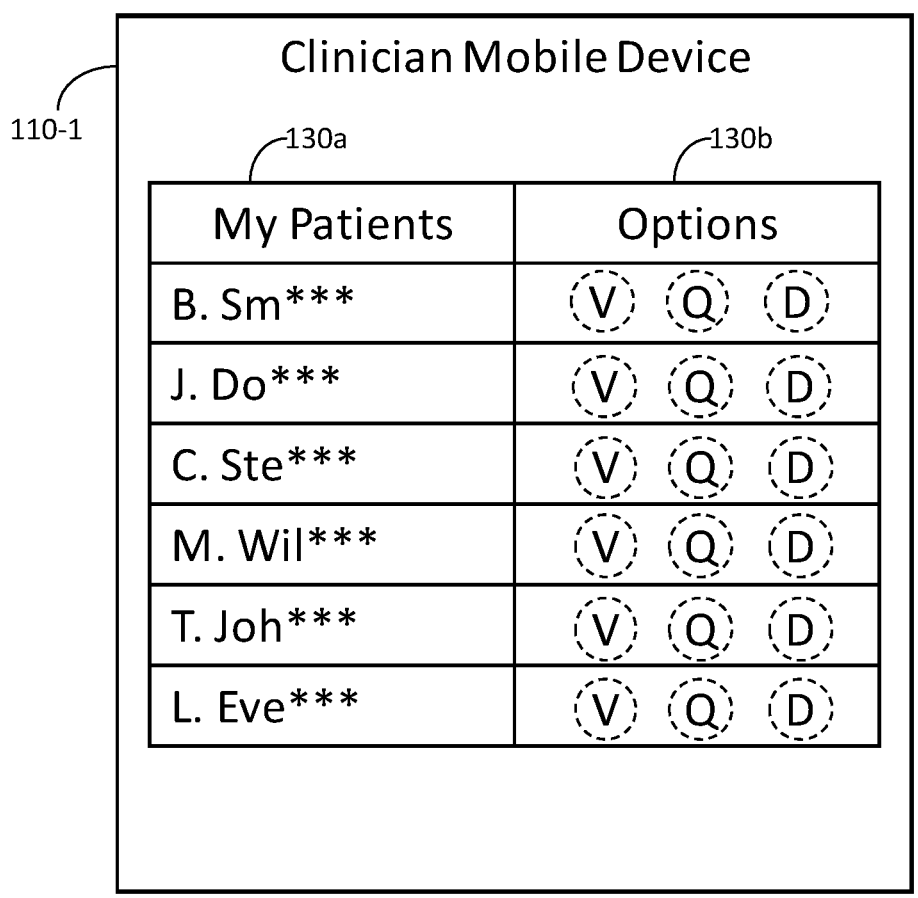

An example GUI with the medication administration functions disabled is shown in FIG. 1C. In FIG. 1C, computing device 110-1 may display a user interface comprising GUI area 130a presenting a list of patients assigned to the clinician associated with the computing device 110-1, and GUI area 130b presenting GUI elements corresponding to administration functions of viewing the ordered medications ("V"), queueing the ordered medications to one or more electronic medication storage cabinets 104 ("Q"), and dispensing the ordered medications from the one or more electronic medication storage cabinets 104 ("D"). In some implementations, the server 108 may be configured to cause the appearance of the GUI to change (e.g., change a perceivable characteristic of a GUI element such as color, image, font, shape, outline style, highlighting, etc.) when the associated medication administration functionality is disabled. For example, as shown in FIG. 1C, when a medication administration functionality is disabled, the associated GUI may be highlighted with a dashed line.

Figure 1D:
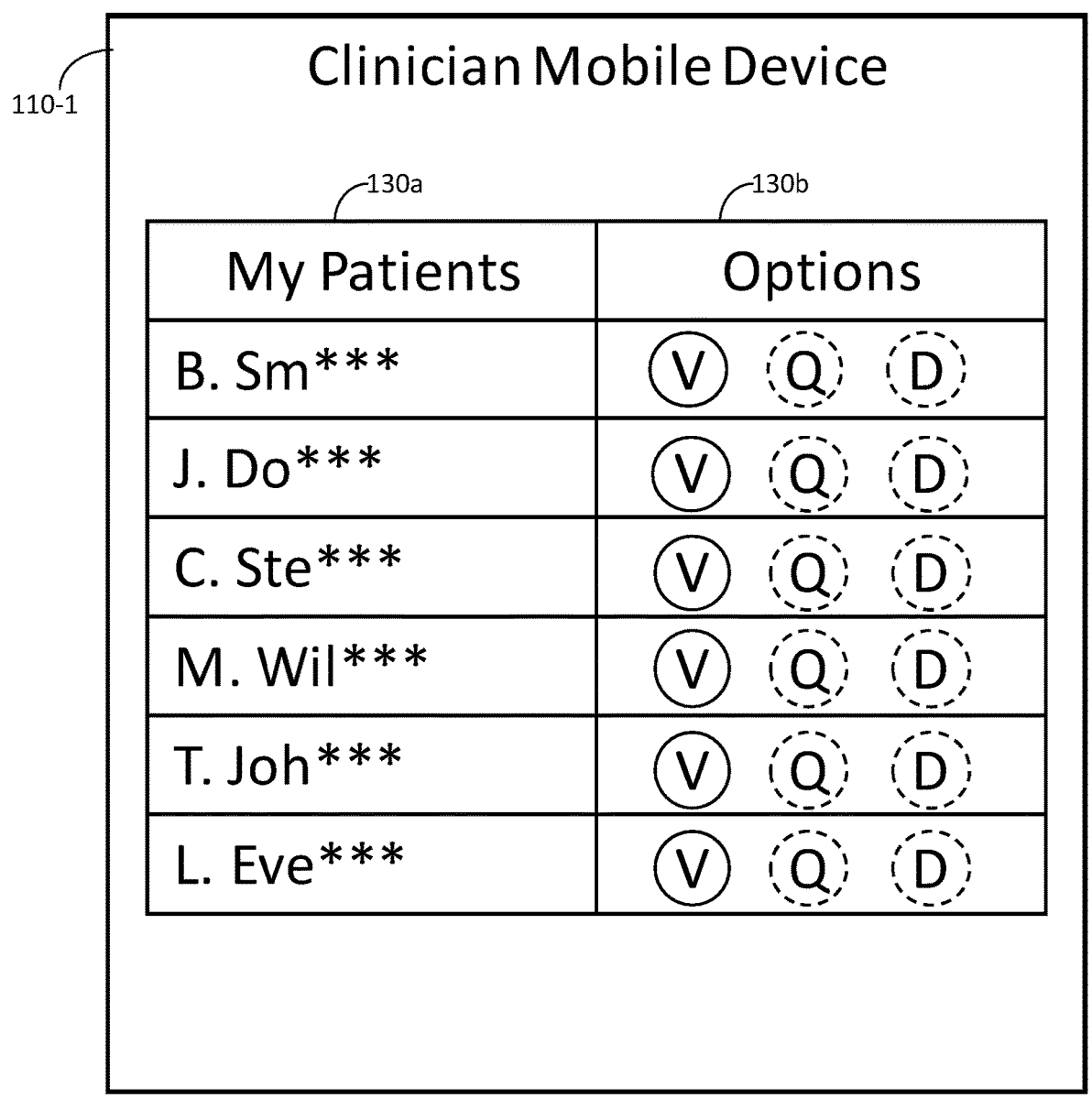

Returning to FIG. 1B, a stored set of rules may indicate that the functionality of viewing ordered medications of a patient (e.g., stored in a storage cabinet for the patient) should be enabled but the functionalities to queue and dispense medications should be disabled, when the computing device 110 is within area 120a, and outside of area 120b and 120c, for example. Then, if the server 108 determines that the computing device 110 is within area 120a and outside of area 120b and 120c, the server 108 may update the permissions to enable functionality of viewing ordered medications for computing device 110. The server 108 may transmit the updated permissions to the computing device 110 to cause the user interfaces associated with the functionality of viewing ordered medications to be enabled. An example of GUI associated with only viewing functionality being enabled for a group of patients is shown in FIG. 1D. As can be seen in FIG. 1D, the GUIs associated with queueing and dispensing functionalities continue to be disabled.

Figure 1E:
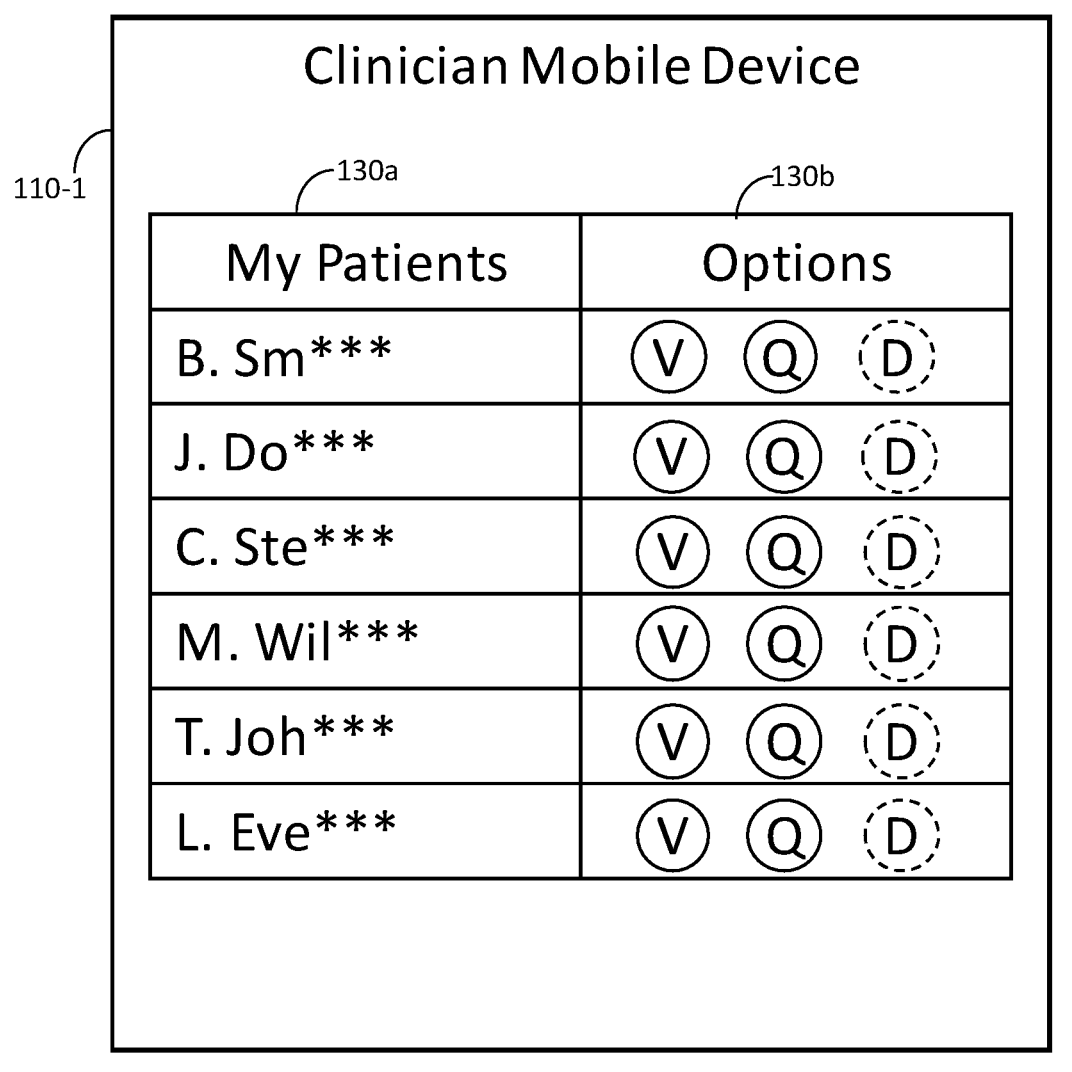

Similarly, if the stored set of rules indicate that the functionality to queue ordered medications to an electronic medication storage cabinet 104 should be enabled and the functionality to dispense the ordered medications should be disabled when the computing device 110 is within threshold area 120b but outside of threshold area 120c, and if the server 108 determines that the computing device 110 is within area 120b but outside of area 120c, then the server 108 may update the permissions to enable queuing functionality and transmit the updated permissions to the computing device 110 to cause the user interfaces associated with the functionality of queuing ordered medications to an electronic storage cabinet 104 to be enabled. An example of a GUI associated with the queuing functionality being enabled is shown in FIG. 1E, where the GUIs associated with the viewing and queuing functionalities are enabled but the GUIs associated with the dispensing functionality is disabled.

Figure 1F:
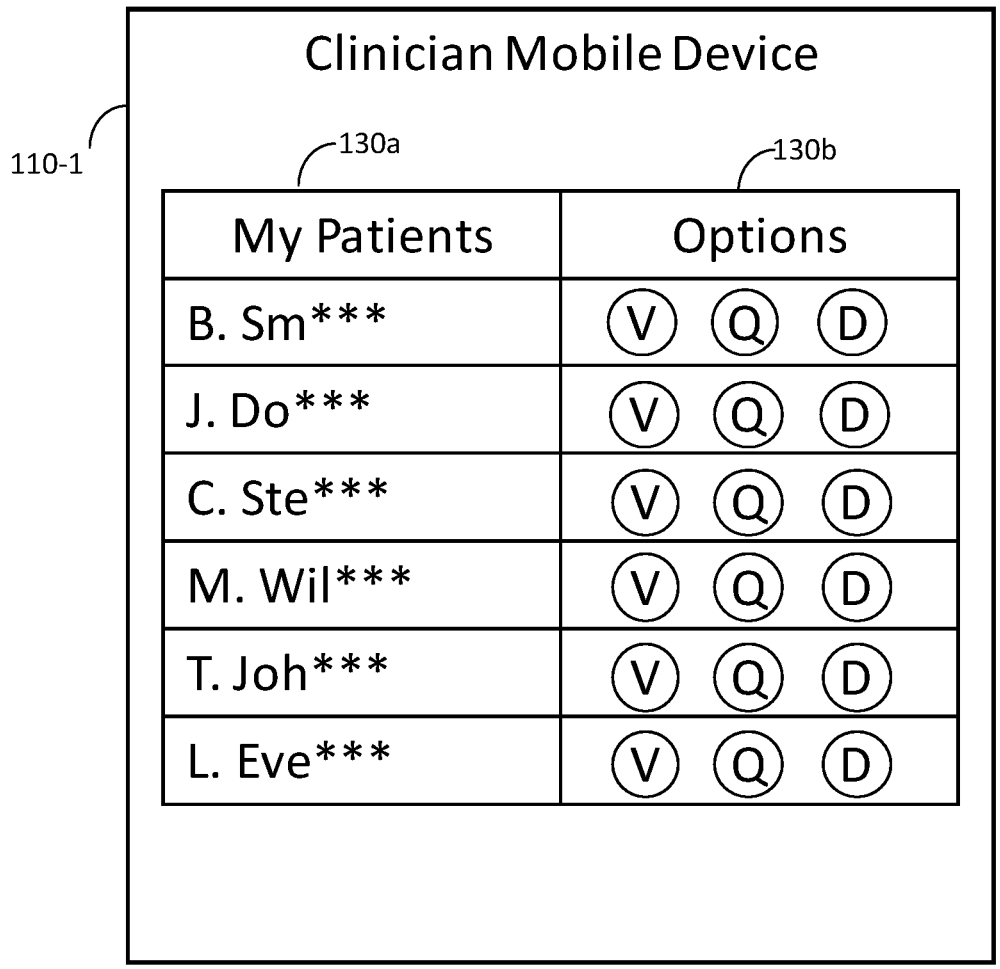
Figure 1G:
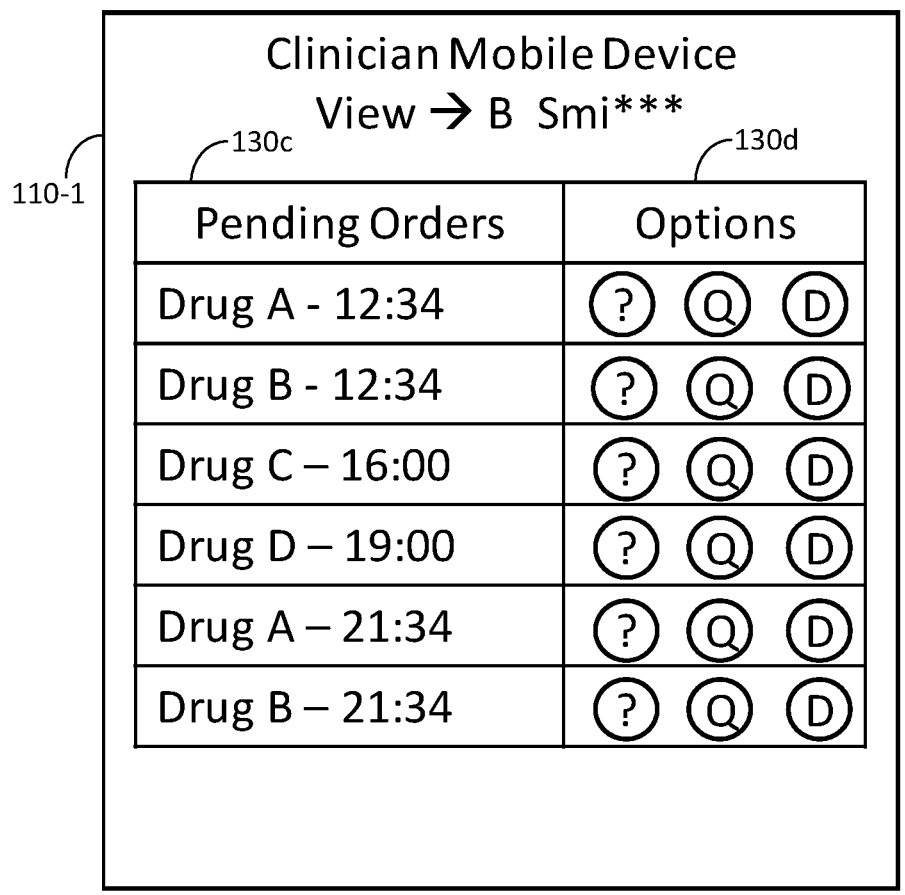

In yet another example, if the stored set of rules indicate that the functionality to dispense ordered medications from an electronic medication storage cabinet 104 should be enabled when the computing device 110 is within threshold area 120c, and if the server 108 determines that the computing device 110 is within area 120c, then the server 108 may update the permissions to enable dispensing functionality and transmit the updated permissions to the computing device 110 to cause the user interfaces associated with the functionality of dispensing ordered medications to an electronic storage cabinet 104 to be enabled. An example of a GUI associated with the dispensing functionality being enabled is shown in FIG. 1F, where the GUIs associated with the viewing, queuing, and dispensing functionalities are enabled. In some implementations, computing devices 110 may present GUIs to allow a clinician to view details of individual ordered medications, queue the individual ordered medications, and dispense the individual ordered medications for a patient. An example of such GUIs are shown by GUI area 130c and GUI area 130d in FIG. 1G. In some implementations, a computing device 110 may display the GUIs shown in FIG. 1G in response to a clinician selecting a name of a patient and/or the GUI associated with the viewing functionality in GUI area 130b.

The server 108 may be configured to receive requests for queuing one or more medications from a computing device in response to the clinician selecting a GUI associated with the queuing functionality. In some implementations, electronic medication storage cabinets 104 may be associated with predetermined areas. For example, as shown in GUI element 130e of FIG. 1H, the electronic medication storage cabinet 104 "ADC Floor 1-Room 1" may be associated with the predetermined area of Room 1 on the first floor of the healthcare organization. Similarly, the electronic medication storage cabinet 104 "ADC Floor 1-Room 2" may be associated with the predetermined area Room 2 on the first floor and the electronic medication storage cabinet 104 "ADC Floor 2-Room 7" may be associated with the predetermined area Room 7 on the second floor. In some implementations, the electronic medication storage systems server 108 may be configured to identify one or more electronic medication storage cabinets 104 based on the predetermined area within which a computing device 110 is located and on whether the one or more medications are stored in the electronic medication storage cabinets 104. In some implementations, the server 108 may be configured to identify, based on a queuing criteria, one or more electronic medication storage cabinets 104 that provide the most efficient and optimized source from which to dispense medications after the medication are queued to that source, referred to herein as "optimal electronic medication storage cabinet." Additional details of identifying the optimal electronic medication storage cabinet may be describe below with reference to FIG. 5. The server 108 may be configured to transmit data related to the identified optimal electronic medication storage cabinet to the computing device 110 to be displayed to the clinician. An example of the optimal electronic medication storage cabinet displayed to a clinician is shown by GUI element 130e in FIG. 1H, where "ADC Floor 1-Room 2" is the optimal electronic medication storage cabinet identified by the server 108 to which the medications ordered for the patient "B. Sm***" should be queued. A clinician may select a different electronic medication storage cabinet 104 than the optimal electronic medication storage cabinet recommended by the server 108 by selecting another GUI item and/or icon in the GUI element 130e. In some implementations, a clinician may transmit an agreement with the recommended optimal electronic medication storage cabinet and/or transmit selection of a different electronic medication storage cabinet 104 by selecting the GUI element 130f.

Figure 1H:
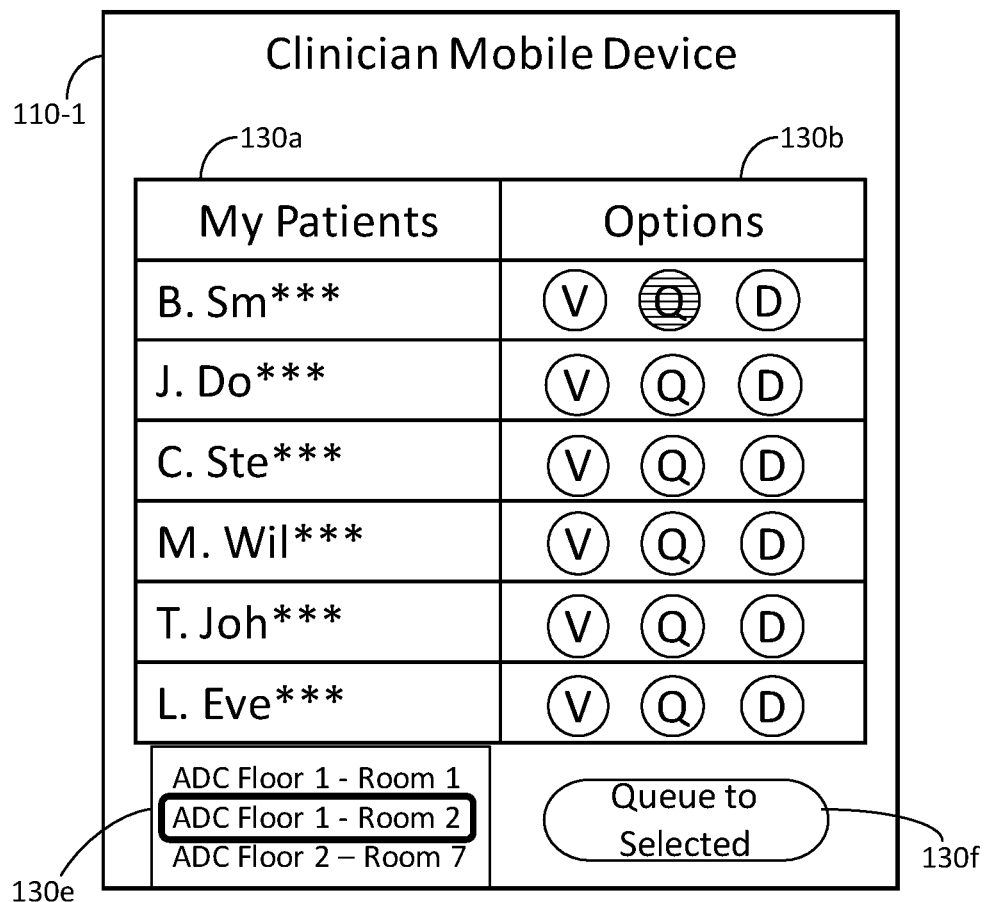
Figure 1I:
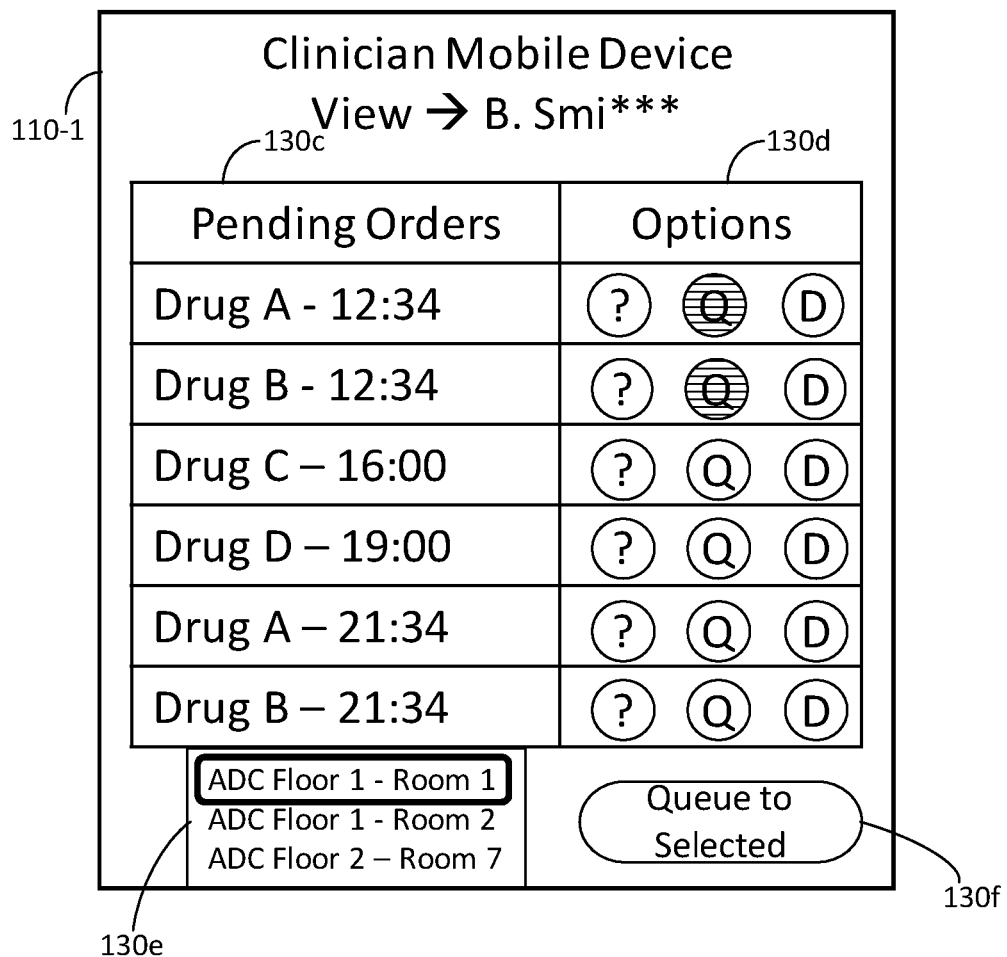

In some implementations, the server 108 may be configured to determine whether all of the ordered medications of a patient may be queued to a single electronic medication storage cabinet 104, and if the server 108 determines that all of the medications can be queued to a single electronic medication storage cabinet 104, then the server 108 may allow a clinician to queue all ordered medications with a single selection, such as via the selection of "Q" in GUI area 130b for patient "B. Sm***" in GUI area 130a of FIG. 1H. In some implementations, if the server 108 determines that all of the ordered medications of a patient cannot be queued to a single electronic medication storage cabinet 104, then the server 108 may transmit an instruction to computing device 110 to display a GUI to prompt the clinician to queue different subsets of ordered medications to different electronic medication storage cabinets 104. An example of a GUI that allows a clinician to select individual medications to be queued is shown by GUI areas 130c and 130d in FIG. 1I. The server 108 may be configured to queue individual ordered medications to one or more electronic medication storage cabinets 104, and may identify one or more optimal electronic medication storage cabinet 104 for different subsets of ordered medications being queued. As can be seen in FIG. 1I, medications "Drug A" and "Drug B" are selected for queueing by a clinician, and the server 108 identified "ADC Floor 1-Room 1" as the optimal electronic medication storage cabinet 104 (as shown by GUI element 130e) to which the medications "Drug A" and "Drug B" should be queued. In some implementations, if the server 108 determines that all of the ordered medications of a patient cannot be queued to a single electronic medication storage cabinet 104, then the server 108 may transmit an instruction to computing device 110 to disable a GUI associated with confirming a selection of an electronic storage cabinet 104, such as the GUI element 130e and/or GUI element 130f.

Figure 2:
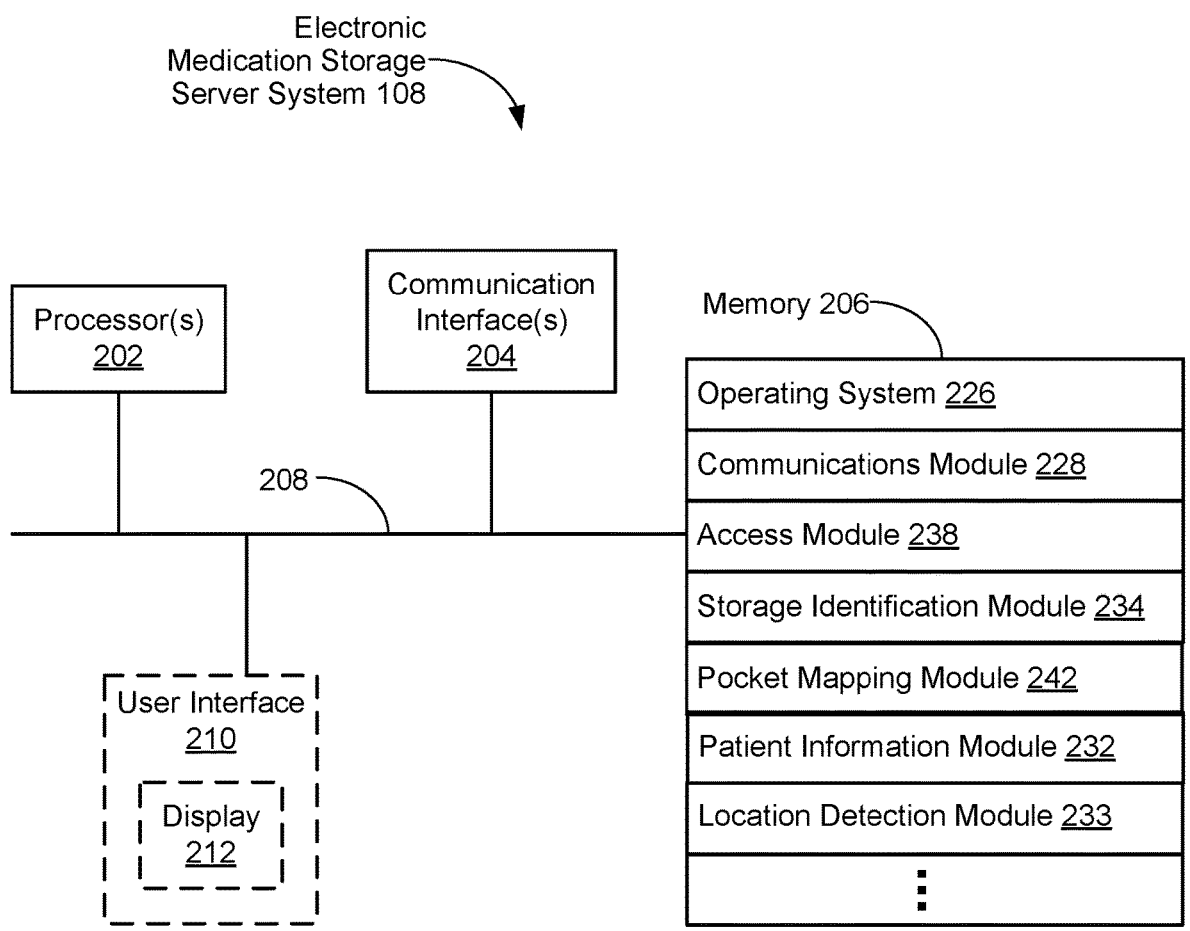
FIG. 2 is a block diagram of an exemplary server system from the architecture of FIG. 1 according to illustrative implementations.

Turning now to FIG. 2, there is shown a block diagram depicting a server 108 in accordance with some implementations. According to various implementations, FIG. 2 may also be representative of a respective computing device 110. The server 108 (or computing device 110) typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. In some implementations, the server 108 may include a user interface unit 210. The user interface unit 210 may include a display device 212. In some implementations, the server 108 may include input devices such as a keyboard, a mouse, a trackpad, and/or input buttons. In some implementations, the display device 212 may include a touch-sensitive surface, in which case the display is a touch-sensitive display.

In some implementations, the server 108 may be configured to receive data related to patients, pockets, movable drawers, and the like, from the electronic medication storage cabinets 104. For example, the server 108 may receive a list of medications stored in a respective cabinet, and a pocket identifier and/or location of each medication stored in the respective cabinet. In some implementations, the server 108 may be configured to transmit data related to optimized processes of dispensing ordered medications from electronic medication storage cabinets 104. The server 108 may be configured to receive data related to ordered medications for patients, for dispensing from electronic medication storage cabinets 104, and the like, from pharmacy information systems 112 and/or health information systems 114. The server 108 may be configured to transmit data related to dispensing of medication in medication containers, status indicating success or failure of dispensing the ordered medication from the electronic medication storage cabinets 104, and the like, to the computing devices 110. In some implementations, the server 108 may be located either on premises of a healthcare organization, remotely hosted by a third-party service provider (e.g., in a cloud computing environment), and/or a combination thereof.

The server 108 may be configured with a mapping algorithm that is configured to identify a location in an electronic medication storage cabinet storing a medication and/or a medicine container containing the medication. In some implementations, the medicine container may be a dynamic pocket described herein. In some implementations, the server 108 may generate a sequence of one or more steps to load the medication and/or the medicine container into the identified location of an electronic medication storage cabinet based on the mapping algorithm. When a request is received for the location of a medication, the server 108 may determine which cabinets 104 contain the medication and/or the drawer and/or pocket of the cabinet in which the medication is currently stored. In some implementations, the server 108 may return the locations to the computing device 110 based on the location of the computing device relative to the determined location(s) of the cabinet(s) storing the medication.

The memory 206 of server 108 (or computing device 110) may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 206 includes one or more storage devices remotely located from the processor(s) 202. The memory 206, or alternatively the non-volatile memory device(s) within the memory 206, includes a non-transitory computer-readable storage medium. In some implementations, the memory 206 or the computer-readable storage medium of the memory 206 stores programs, modules, and/or data structures that may be used for the performing one or more operations of the server system 108. The electronic storage system server 108 may execute the mapping algorithm based on one or more modules described herein and/or included in the memory 206. For example, the memory 206 may include programs, modules, and/or data structures for an operating system 226, a network communication module 228, a patient information module 232, an access device module 238, a storage identification module 234, a pocket mapping module 242.

In some implementations, the operating system 226 module may include procedures for handling various basic system services and for performing hardware dependent tasks. The network communication module 228 may be configured for connecting the server 108 to other computing devices via the one or more communication network interfaces 204 (wired or wireless) and one or more communication networks 106. The patient information module 232 may be configured to store data related to patients including, but not limited to, medical history, prescription medication, allergies, and the like. The patient information module 232 may be configured to associate a patient with an electronic medication storage cabinet 104, and store the association in memory 206. The access module 238 may be configured to grant, deny, and/or modify access to the server 108 and/or one or other computing systems or devices communicatively coupled to the server 108. In some implementations, a location detection module 233 may be configured with GPS sensing technology and devices for determining a current coordinate location of the computing device, and reporting the location to software applications operating on the device.

The storage identification module 234 may be configured to store, maintain, and/or update data related to the contents of every pocket for each electronic medication storage cabinet 104 communicatively coupled to the server 108. The storage identification module 234 may be configured to store, maintain, and/or update data related to every empty pocket for each electronic medication storage cabinet 104 communicatively coupled to the server 108. The server 108 may receive data related to contents of pocket from the electronic medication storage cabinets 104, and the storage identification module 234 may be configured to maintain and/or update data related to contents of pocket based on the data received from the electronic medication storage cabinets 104.

For each electronic medication storage cabinet 104 communicatively coupled to the server 108, the pocket mapping module 242 may be configured to associate the pockets of each movable drawer with corresponding locations in the movable drawer, and store the associations in memory 206.

In some implementations, the pocket mapping module 242 may be configured to receive data related to sensors with their locations in drawers for each electronic medication storage cabinet 104, and based on the mapping, the pocket mapping module 242 may be configured to determine locations of pockets within the drawers.

Each of the above identified modules and applications corresponds to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various implementations. In some implementations, the memory 206 may store a subset of the modules and data structures identified above. In some implementations, the memory 206 may store additional modules and data structures not described above. Processors 202 may be configured to execute the above identified modules for performing the one or more above-described functions and/or techniques of enabling and/or disabling one or more medication administration functions for a computing device based on the location of the computing device, as described herein with reference to FIGS. 4-7.

Figure 3:
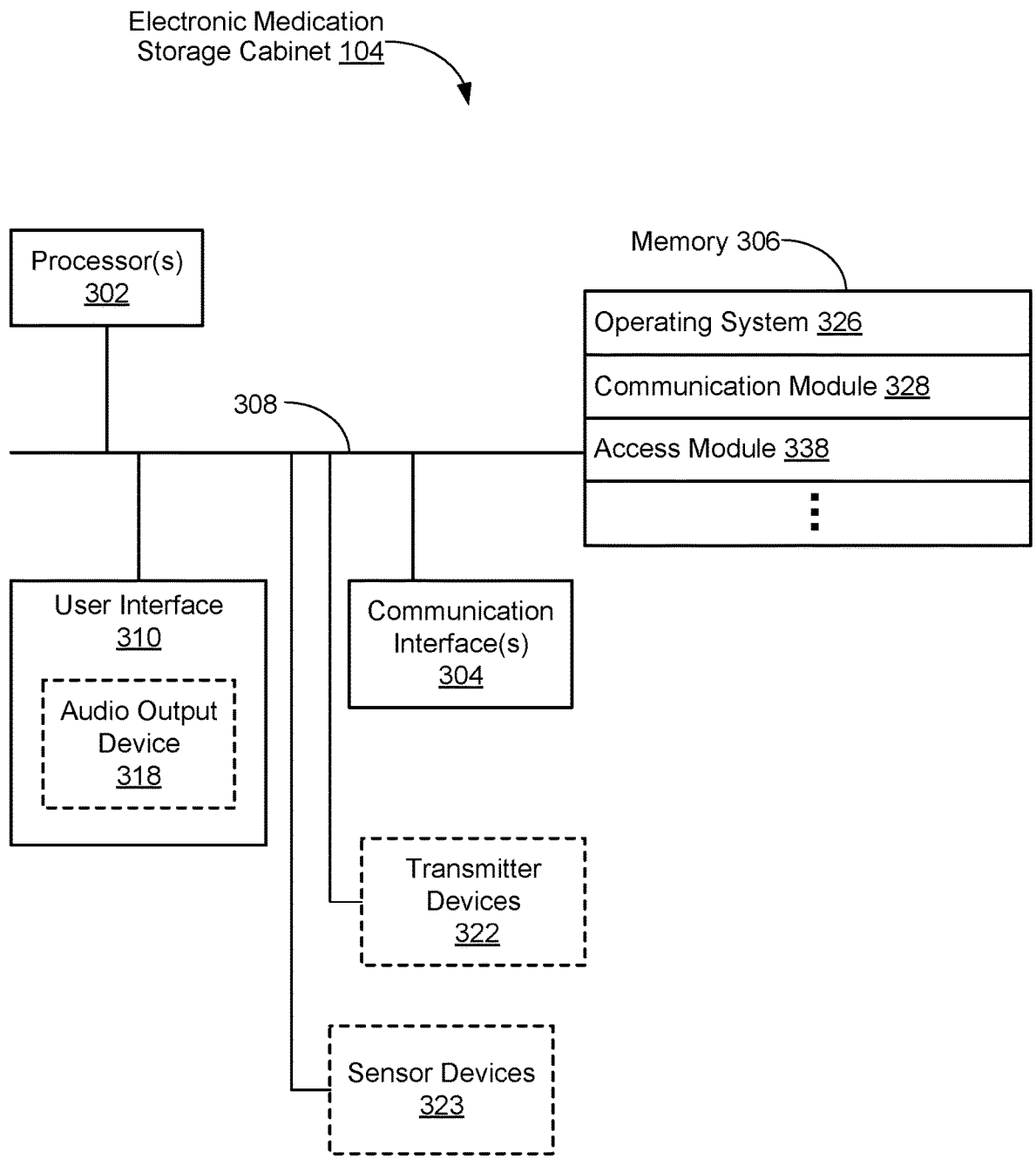
FIG. 3 is a block diagram of an exemplary electronic medication storage device from the architecture of FIG. 1 according to illustrative implementations.

Turning now to FIG. 3, there is shown a block diagram depicting an electronic medication storage cabinet 104. An electronic medication storage cabinet 104 may include one or more processors 302, one or more network or communications interfaces 304 (wired or wireless), memory 306, one or more communication buses 308, a user interface unit 310, transmitter devices 322, sensor devices 323. The one or more processors 302, the one or more network or communication interfaces 304, memory 306, and the user interface unit 310 may be configured to communicate with one another via the one or more communication buses 308. In some implementations, the communication buses 308 may include circuitry (sometimes called a chipset) that interconnects and controls communications between components of the electronic medication storage cabinet 104. In some implementations, the user interface unit 310 may include an audio output device 318. The one or more processor 302 may be configured to generate one or more different sounds via the audio output device 318 for different alarms with which the electronic medication storage cabinet 104 is configured.

The memory 306 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. In some implementations, the memory 306 includes one or more storage devices remotely located from the processor(s) 302. The memory 306, or alternatively the non-volatile memory device(s) within the memory 306, includes a non-transitory computer-readable storage medium. In some implementations, the memory 306 or the computer-readable storage medium of the memory 306 stores the programs, modules, and data structures that may be used for performing operations of the electronic medication storage cabinets 104 and for performing techniques described herein for dispensing one or more medications from an electronic medication storage cabinet. The memory 306 may include an operating system 326, a network communication module 328, a storage identification module 334, an access module 338, and/or a patient information module 348.

The operating system 326 may be configured to perform procedures of execution of various system services of the electronic medication storage cabinet 104, including, but not limited to, hardware, and software dependent tasks. The network communication module 328 may be configured to execute instructions to connect the electronic medication storage cabinet 104 to one or more other computing devices, such as the server 108, computing devices 110, and the like, via the one or more communication interfaces 304 and communication networks, such as the communication network 106. The access module 338 may be configured grant, deny, and/or modify access to the electronic medication storage cabinet 104. For example, the access module 338 may be configured to grant or deny access to the electronic medication storage cabinet 104 based on received login credentials for the electronic medication storage cabinet 104.

In some implementations, one or more sensor devices 323 and/or one or more transmitter devices 322 may be configured to detect broadcasting of wireless communication signals (e.g., Bluetooth signals, and the like) from one or more devices (e.g., computing devices 110) and transmit and/or broadcast a wireless communication signal (e.g., Bluetooth signal, and the like) to one or more devices (e.g., computing devices 110). In some implementations, in response to detecting the wireless communication signal, the one or more processors 302 of the electronic medication storage cabinets 104 may be configured to initiate and/or establish a wireless connection with a device broadcasting the wireless communication signal. In some implementations, the one or more processors 302 of the electronic medication storage cabinet 104 may be configured to initiate and/or establish a wireless connection with a device broadcasting the wireless communication signal after receiving a passphrase from the computing device 110. In some implementations, in response to detecting the wireless communication signal, the one or more processors 302 may be configured to transmit and/or cause to transmit a wireless communication signal via the one or more transmitter devices 322 and/or sensor devices 323.

Each of the above identified modules and applications corresponds to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various implementations. In some implementations, the memory 206 and/or the memory 306 store a subset of the modules and data structures identified above. In some implementations, the memory 206 and/or the memory 306 stores additional modules and data structures not described above.

Figure 4:
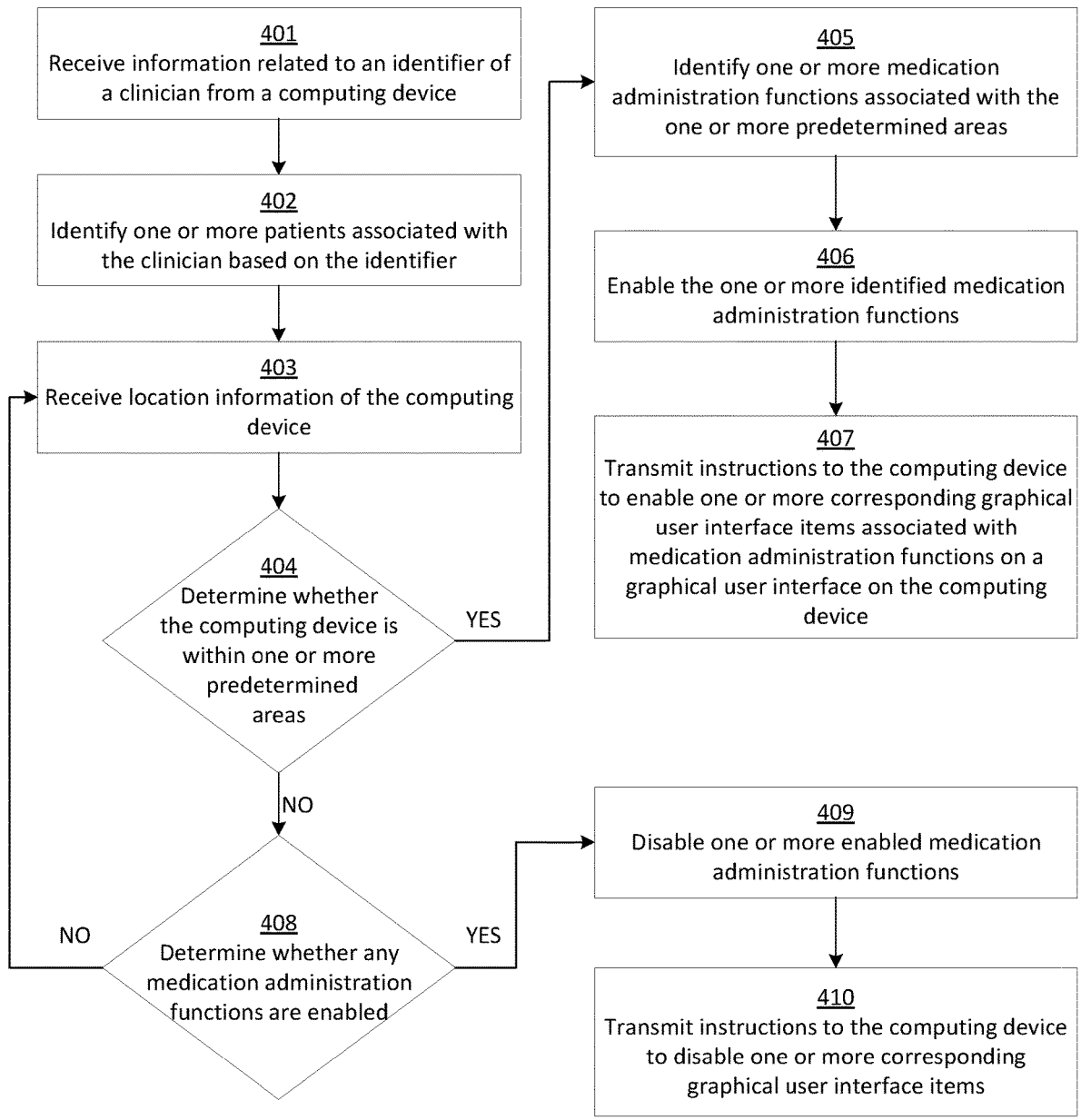
FIG. 4 is a flow chart of an example process of enabling and/or disabling medication administration functions based on location of a computing device, according to illustrative implementations.

Turning now to FIG. 4, there is shown a flowchart illustrating a process of enabling and/or disabling one or more medication administration functions based on a location of a computing device. For the purpose of illustrating a clear example, components of the network architecture 100, shown and described with reference to FIG. 1A, components of the server 108, shown and described with reference to FIG. 2, and components of the electronic medication storage cabinets 104, shown and described with reference to FIG. 3 may be used to describe the process of enabling and/or disabling one or more medication administration functions based on a current location of a computing device.

The method 400 includes receiving, by one or more processors 202 of the server 108, information related to an identifier of the clinician from a computing device (block 401). As described above, a clinician may login and/or sign-in on an application executed on a computing device 110 to receive information related to patients assigned to the clinician and/or administer one or more medications to an assigned patient. In response to the computing device 110 receiving an identifier (e.g., username, password, and the like) of the clinician, the computing device 110 transmits the identifier to the server 108. In some implementations, the server 108 associates the clinician with the computing device 110 by storing the identifier of the clinician in association with an identifier of the computing device 110 (e.g., a media access control (MAC) address).

The server 108 identifies one or more patients associated with the clinician based on the identifier of the clinician (block 402). In some implementations, the server 108 may receive lists of patients assigned to different clinicians, and the server 108 may store a list of assigned patients in association with an identifier of a clinician. In some implementations, the server 108 may transmit the list of patients to the computing device 110. In some implementations, the server 108 may transmit an instruction to cause the list of patients to be displayed on a display device associated with the computing device 110. For example, the server 108 may transmit an instruction to cause the list of patients to be displayed in a GUI, such as GUI area 130*a*. In some implementations, the server 108 may transmit any pending medication orders for any of the assigned patients to the computing device 110. Examples of pending medication orders may include, but are not limited to, medication orders that are not dispensed from an electronic medication storage cabinet and/or administered to the corresponding patient. As described above, the server 108 may enable functionality on the computing device 110 for viewing the transmitted medication orders based on the location information of the computing device 110 (e.g., based on whether the computing device 110 is within a predetermined area associated with the viewing functionality). The server 108 receives location information of the computing device 110 (block 403). As described above, examples of location information include, but are not limited to, wireless access point information, internet protocol address, geospatial coordinates, data from a global positioning system (GPS) sensors of computing devices 110, and the like. In some implementations, the server 108 may be configured to determine a physical distance of the computing device 110 with reference to another structure (e.g., building of the healthcare organization, an area/portion of a floor of a building, and the like) and/or device (e.g., an electronic medication storage cabinet 104, another computing device, and the like) based on the location information of the computing device 110.

The server 108 determines whether the computing device is within one or more predetermined areas (block 404). As described above, and with reference to FIG. 1B, the server 108 may receive and/or store a set of rules and/or configuration data that indicates the one or more threshold areas, and determine whether the computing device 110 is within one or more of the threshold areas based on the location information of the computing device 110 and the stored set of rules. If the server 108 determines that the computing device 110 is within one or more predetermined areas ('YES' at block 404), then the method 400 proceeds to block 405. The server 108 identifies one or more medication administration functions associated with the one or more predetermined areas (block 405). The server 108 may identify the one or more administration functions associated with a predetermined area based on the stored set of rules. For example, using the areas described above with reference to FIG. 1B, the stored set of rules may indicate that when a computing device is in area 120*b* and outside of area 120*c*, then the medication administration function of viewing and queuing an ordered medication can be enabled but not the function of dispensing the medication, then the server 108 may be configured to determine that the medication administration functions of viewing and queuing an ordered medication are associated with the area 120*b*. Similarly, if the stored set of rules indicate that only the viewing function can be enabled when the computing device 110 is in area 120*a* and outside of area 120*b*, then the server 108 may be configured to determine that the medication administration functions of viewing an ordered medication is associated with the area 120*a*.

The server 108 enables the one or more identified medication administration functions (block 406). The server 108 may store a set of permissions for one or more medication administration functions in association with identifiers of computing devices 110, and the server 108 may enable a medication administration function for a computing device 110 by updating one or more permissions associated with that function for the computing device 110. The server 108 transmits instructions to the computing device to enable one or more corresponding GUI items associated with the medication administration functions on a GUI on the computing device 110 (block 407). Examples of one or more enabled GUI items associated with the medication administration are described above with references to FIGS. 1D-1I.

In some implementations, the server 108 may identify one or more medication administration functions that are not associated with the predetermined threshold area in which the computing device 110 is currently located. For example, using the areas described above with reference to FIG. 1B, if the computing device 110 was previously in threshold area 120*c* and is currently within threshold area 120*a* but outside of threshold area 120*b*, and the stored rules and/or configuration data indicate that the medication administration functions of queueing and dispensing ordered medications should be disabled for a computing device within threshold area 120*a* but outside of threshold area 120*b*, then the server 108 may identify that queuing and dispensing functions are not associated with the threshold area 120*a* and may update corresponding permissions of the queuing and dispensing functions to disable them for the computing device 110. The server 108 may transmit instructions to the computing device 110 to disable one or more corresponding GUI items associated with the queuing and dispensing functions on the GUI on the computing device 110.

Returning to block 404, if the server 108 determines that the computing device 110 is not within any of the one or more predetermined areas ('YES' at block 404), then the method 400 proceeds to block 408. The server 108 determines whether any medication administration functions are enabled for the computing device 110 (block 408). As described above, the server 108 updates stored permissions when a medication administration function is enabled for a computing device 110, and the server 108 determines whether one or medication administration functions were previously enabled based on the stored permissions.

If the server 108 determines that a medication administration function is enabled ('YES' at block 408), then the method 400 proceeds to block 409. The server 108 disables the one or more enabled medication administration functions (block 409). The server 108 may be configured to disable the one or more medication administration functions by updating the permissions of the one or more enabled medication administration functions to deny access to the functions. The server 108 transmits instructions to the computing device 110 to disable one or more corresponding GUI items associated with the medication administration functions on a GUI on the computing device 110 (block 410). Returning to block 408, if the server 108 determines that medication administration functions are not enabled ('NO' at block 408), then the method 400 proceeds to block 403.

Figure 5:
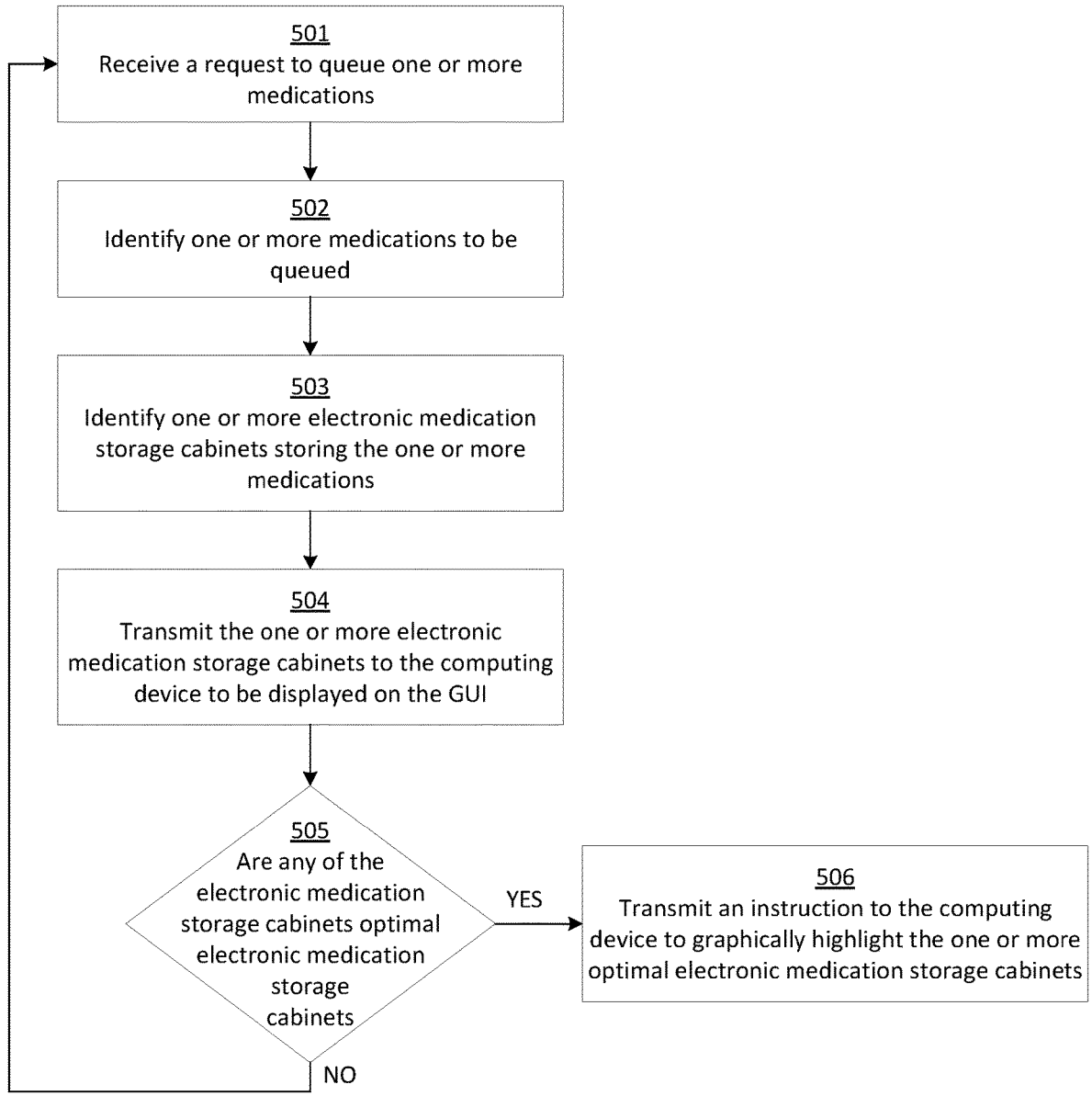
FIG. 5 is a flow chart of an example process of identifying electronic medication storage cabinet based on a request for queuing medications, according to illustrative implementations.

Turning now to FIG. 5, there is shown a flowchart illustrating a process of identifying an optimal electronic medication storage cabinet for queuing of medications. For the purpose of illustrating a clear example, components of the network architecture 100, shown and described with reference to FIG. 1A, components of the server 108, shown and described with reference to FIG. 2, and components of the electronic medication storage cabinets 104, shown and described with reference to FIG. 3 may be used to describe the process of identifying an optimal electronic medication storage cabinet for queuing of medications.

The method 500 includes receiving, by one or more processors 202 of the server 108, a request to queue one or more medications from a computing device (block 501). The server 108 may receive the request to queue in response to a selection by a clinician on the computing device 110 to queue the one or more ordered medications. The server 108 identifies the one or more medications to be queued based on the received request (block 502). The server 108 identifies one or more electronic medication storage cabinets storing the one or more identified medications (block 503). As described above, a mapping and/or an association between medications and electronic medication storage cabinets 104 and pockets of the electronic medication storage cabinets 104 is stored in one or more data storage units of the server 108, and the server 108 may be configured to identify one or more electronic medication storage cabinets 104 based on the mapping and/or association between medications and the electronic medication storage cabinets 104.

The server 108 transmits the one or more identified electronic medication storage cabinets to the computing device to be displayed on the GUI (block 504). The server 108 determines whether any of the identified electronic medication storage cabinets are optimal electronic medication storage cabinets (block 505). As described above, the server 108 determines whether an electronic medication storage cabinet 104 is an optimal electronic medication storage cabinet based on a queuing criteria. A queuing criteria may be a predetermined criteria for identifying one or more optimal electronic medication storage cabinets to which medications should be queued. Example factors of the queuing criteria may include, but are not limited to, threshold percentage (e.g., 100 percent, 75 percent, and the like) of the identified medications are available in an electronic medication storage cabinet 104, expiration dates of the medications in an electronic medication storage cabinet 104, distance from a patient's location to an electronic medication storage cabinet 104 storing one or more medications ordered for the patient, distance from a clinician to an electronic medication storage cabinet 104 storing one or more ordered medications for dispensing by the clinician or to a patient associated with the clinician, whether patient-specific medications are stored in the electronic medication storage cabinet 104, and the like.

For example, if five medications are queued for a patient, and a first electronic medication storage cabinet 104 comprises three of the five medications, a second electronic medication storage cabinet 104 comprises the remaining two, and a third electronic medication storage cabinet 104 comprises all five medications, then the server 108 may identify the third electronic medication storage cabinet 104 as the optimal electronic medication storage cabinet. Similarly, if a distance of the first electronic medication storage cabinet 104 and the second electronic medication storage cabinet 104 to the patient satisfy a threshold distance, and the distance of the third electronic medication storage cabinet does not satisfy the threshold distance, then the server 108 may identify the first and the second electronic medication storage cabinets 104 as the optimal electronic medication storage cabinets 104.

If the server 108 identifies one or more electronic medication storage cabinets 104 as optimal electronic medication storage cabinets ('YES' at block 505), then the method 500 proceeds to block 506. The server 108 transmits an instruction to the computing device to cause the computing device to graphically highlight the one or more optimal electronic medication storage cabinets (block 506). Examples of the one or more optimal electronic medication storage cabinets graphically highlighted are shown in the GUIs of FIG. 1H and FIG. 1I and described above. If the server 108 does not identify an optimal electronic medication storage cabinets ('NO' at block 505), then the method 500 proceeds to block 501.

Figure 6:
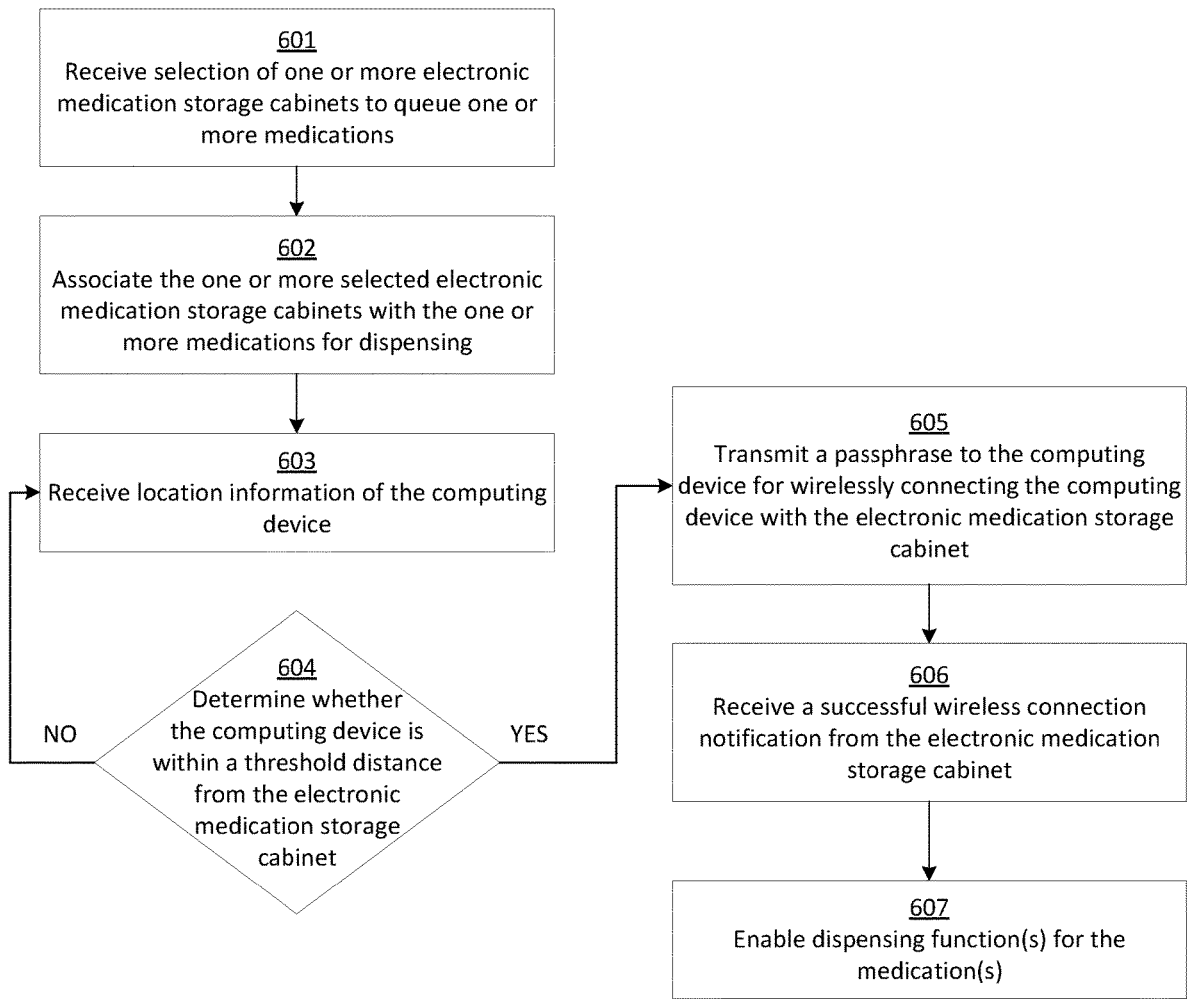
FIG. 6 is a flow chart of an example process of enabling a medication dispensing from an electronic medication storage cabinet, according to illustrative implementations.

Turning now to FIG. 6, there is shown a flowchart illustrating a process of enabling dispensing of medications at an electronic medication storage cabinet. For the purpose of illustrating a clear example, components of the network architecture 100, shown and described with reference to FIG. 1A, components of the server 108, shown and described with reference to FIG. 2, and components of the electronic medication storage cabinets 104, shown and described with reference to FIG. 3 may be used to describe the process of enabling dispensing of medications at an electronic medication storage cabinet.

The method 600 includes receiving, by one or more processors 202 of the server 108, a selection of one or more electronic medication storage cabinets to queue one or more medications from a computing device 110 (block 601). As described above, in some implementations, one or more medication administration functions may be associated with an electronic medication storage cabinet. For example, queuing of ordered medications function may be associated with an electronic medication storage cabinet to which the ordered medications are queued. Similarly, dispensing of ordered medications function may be associated with the electronic medication storage cabinet from which the ordered medications are queued to be dispensed. The server 108 associates the one or more selected electronic medication storage cabinets with the one or more medications for dispensing of the medications (block 602). The server 108 stores the association in one or more data storage units associated with the server 108. The server 108 receives location information of the computing device 110 (block 603).

The server 108 determines whether the computing device 110 is within a threshold distance from the one or more selected electronic medication storage cabinets 104 (block 604). In some implementations, such a predetermined distance may be greater than the above descried threshold area specified by the healthcare organization to enable the dispensing functions for a computing device 110. If the server 108 determines that the computing device 108 is within the threshold distance from the electronic medication storage cabinet ('YES' at block 604), then the method 600 proceeds to block 605. The server 108 transmits a passphrase to the computing device for wirelessly connecting the computing device with the electronic medication storage cabinet (block 605). The computing device 110 may transmit the received passphrase to the electronic medication storage cabinet 104 to establish the wireless connection with the electronic medication storage cabinet 104. The passphrase may be a valid passphrase only for a predetermined period of time, and become an invalid passphrase when the predetermined period of time expires.

In some implementations, the computing device 110 may establish a wireless connection with the electronic medication storage cabinet 104 without providing a passphrase to the electronic medication storage cabinet 104. For example, the computing device 110 may automatically initiate a pairing process with the electronic medication storage cabinet 104 using a wireless communication protocol, such as Bluetooth, when the distance between the computing device 110 and the electronic medication storage cabinet 104 satisfy certain threshold distance, such as the distance specified by the wireless communication protocol. The electronic medication storage cabinet 104 may transmit a message to server 108 indicating a successful wireless connection when a wireless connection between the electronic medication storage cabinet 104 and the computing device 110 is successfully established.

The server 108 receives a successful wireless connection from the electronic medication storage cabinet 104 (block 606). The server 108 enables one or more dispensing functions for the computing device 110 (block 607). In some implementations, the server 108 may enable the one or more dispensing functions after it determines that the computing device 110 is within a threshold area that is associated with the dispensing functions. For example, using the example described above in FIG. 1B, the server 108 may determine, based on any new location information, whether the computing device 110 is within the threshold area 120c, prior to enabling the one or more dispensing functions, and enable those dispensing functions only after determining that the computing device 110 is within the threshold area 120c.

In some implementations, a clinician may initiate the process of dispensing an ordered medication by providing an input to the computing device 110 (e.g., selecting the corresponding graphical item for the ordered medication(s) via the GUI) to transmit a request to the server 108, and the computing device 110 may transmit the selection and/or a message indicating the selection to the server 108. In response to receiving the message and/or request to dispense the ordered medications, the server 108 may identify one or more pockets and/or pocket locations in the electronic medication storage cabinet 104 that comprise the ordered medication based on the above described stored mapping between medications and pockets of electronic medication storage cabinets 104. The server 108 may transmit the identified one or more pockets and/or pocket locations to the electronic medication storage cabinet 104. The server 108 may transmit instructions to dispense the ordered medications to the electronic medication storage cabinet 104 to cause the electronic medication storage cabinet 104 to initiate the process of dispensing medications. In some implementations, in response to receiving instructions to dispense the ordered medications, the electronic medication storage cabinets 104 may be configured to open a drawer comprising a pocket and/or location storing a first medication among the set of medications to be dispensed from the electronic medication storage cabinet 104.

In some implementations, the computing device 110 may transmit a medication dispensing instruction for a set of medications directly to the electronic medication storage cabinet 104 that is wirelessly connected with the computing device 110. In response to receiving the medication dispensing instruction, the electronic medication storage cabinet 104 may transmit the set of medications and a request for locations and/or pockets storing the set of medications in the electronic medication storage cabinet 104 to the server 108. The server 108, in response to receiving the request, may identify locations and/or pockets storing the medications in the electronic medication storage cabinet 104 based on the stored mapping between the locations and/or pockets and identifiers of the medications, and transmit the identified locations and/or pockets to the electronic medication storage cabinet 104. In some implementations, the server 108 may transmit an instruction to the electronic medication storage cabinet 104 to cause one or more drawers of the electronic medication storage cabinet 104 that comprises the one or more identified pockets to open. In some implementations, the server 108 may transmit the instruction to cause the one or more drawers to open when the computing device 110 is within a threshold area and/or threshold distance from the electronic medication storage cabinet 104. In some implementations, the threshold area and/or threshold distance can be the same threshold area and/or threshold distance as the above described threshold area or threshold distance to transmit the passphrase to the computing device 110, for example, with reference to FIG. 6.

Figure 7A:
FIGS. 7A-7C illustrate example communication flows between the various components of the network architecture, according to illustrative implementations.
Figure 7B:
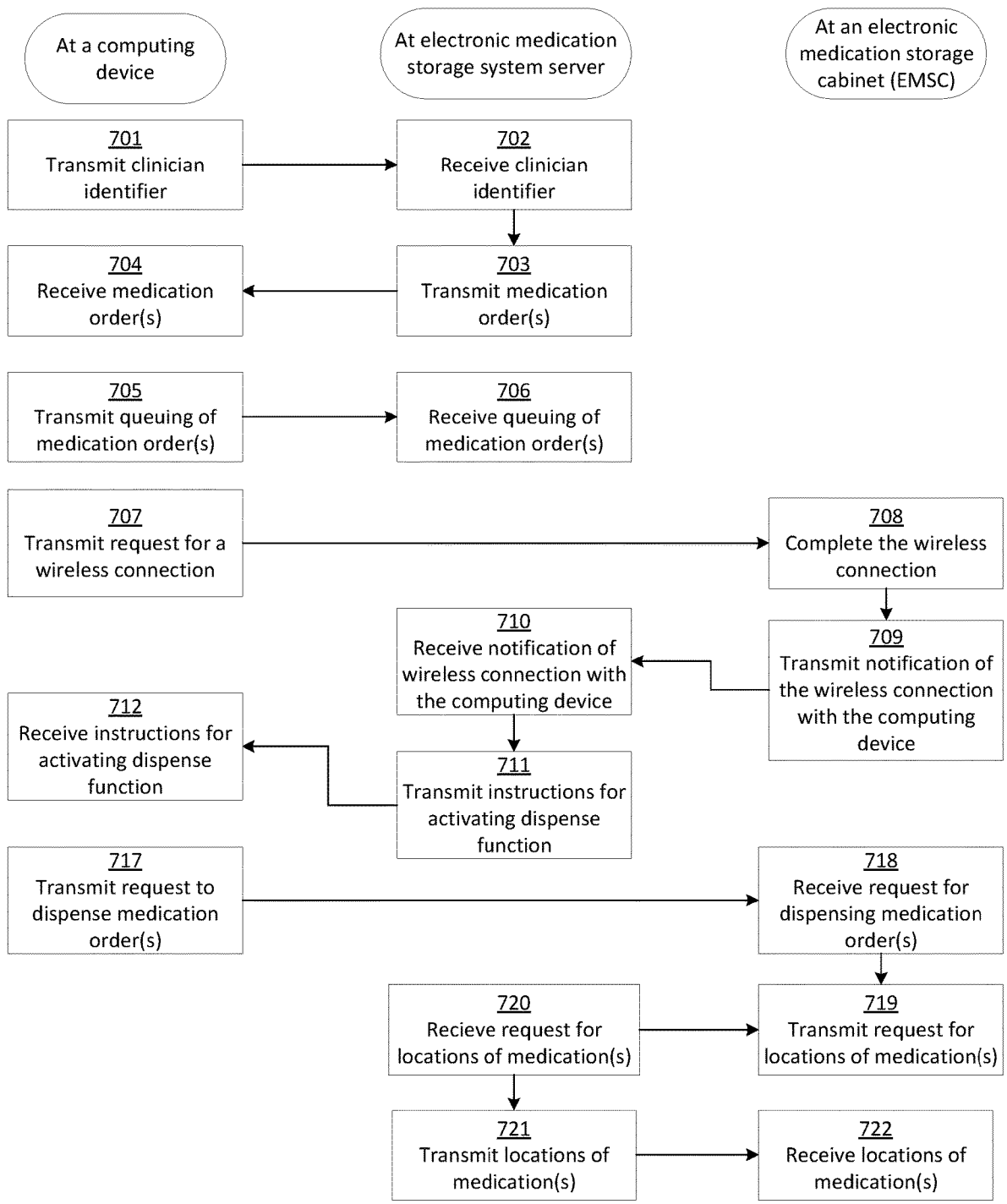

Turning now to FIG. 7A, there are shown example communications between the various components of network architecture 100, such as a computing device 110, an server 108, and an electronic medication storage cabinet 104 for implementing one or more of techniques related to functionalities of above described medication administration, such as viewing, queuing, and/or dispensing medications.

For example, a computing device 110 may transmit a clinician identifier to the server 108 in response to a clinician logging into an application executing on the computing device 110 (block 701). Additional details of the clinician logging into the application and the computing device 110 transmitting a clinician identifier to the server 108 are described above, for example, with reference to FIGS. 1B-II, and 4. The server 108 receives the clinician identifier (block 702) and in response may identify patients assigned to the clinician and medications ordered and/or pending for the identified patients. The server 108 may transmit the identified medication orders to the computing device 110 (block 703). Additional details of the server 108 identifying ordered and/or pending medications for patients are described above, for example, with reference to FIGS. 1B-II and 4.

As described above, the computing device 110 may receive instructions from server 108 to activate and/or enable one or more medication administration functions (e.g., queuing medication function) on the computing device 110 based on the location of the computing device 110. In response to the receiving the instructions, one or more processors of the computing device 110 may enable user interfaces (e.g., a graphical icon, a graphical item, and the like) configured for accepting inputs from a user (e.g., a clinician) of the computing device 110 and associated with the one or more medication administration function (e.g., queuing medication function) to activate and/or enable the one or more medication administration functions on the computing device 110. Blocks 705-706 in FIG. 7A show example communications between the computing device 110 and the server 108 for queuing one or more ordered medications to an electronic medication storage cabinet 104. After the queuing function is activated and/or enabled on the computing device 110, the computing device 110 may receive inputs from a clinician selecting one or more of the medications ordered for one or more patients to be queued to one or more electronic medication storage cabinets 104. The computing device 110, in response to such inputs, may transmit the request for queuing the selected medications to the server 108 (block 705). In some implementations, the computing device 110 may transmit an identifier of each of the ordered medication selected for queuing and an identifier of the electronic medication storage cabinet 104 to which the ordered medication is queued. The server 108 receives the request to queue the medications selected by the clinician (block 706). Additional details of queueing medications and associating the queued medications are described above, for example, with reference to FIGS. 5 and 1B-1I.

Blocks 707-712 in FIG. 7A show example communications between the computing device 110, the server 108, and an electronic medication storage cabinet 104 for activating and/or enabling medication dispensing function on the computing device 110. As described above, in some implementations, the computing device 110 may initiate the process of establishing a wireless connection with an electronic medication storage cabinet 104 using a wireless communication protocol (e.g., pairing with the electronic medication storage cabinet 104 via Bluetooth protocol) by transmitting a request for a wireless connection (block 707) when the computing device 110 is within a predetermined threshold distance of the electronic medication storage cabinet 104. The computing device 110 may transmit an identifier of the computing device 110 to the electronic medication storage cabinet 104 when transmitting the request for the wireless connection (e.g., including the computing device 110's identifier in the request to the electronic medication storage cabinet 104).

The electronic medication storage cabinet 104 may receive the request for wireless connection and complete the wireless connection process by establishing a wireless connection with the computing device 110 (block 708). The electronic medication storage cabinet 104 may be configured to use the computing device 110's identifier in establishing the wireless connection with the computing device 110. The electronic medication storage cabinet 104 may transmit a message and/or a notification to the server 108 notifying the server 108 of the wireless connection with the computing device 110 (block 709). The electronic medication storage cabinet 104 may transmit the identifier of the computing device 110 to the server 108 to identify the computing device 110 with which the wireless connection is established. Additional details of establishing a wireless connection between a computing device 110 and an electronic medication storage cabinet 104 are described above, for example, with reference to FIG. 6. The server 108 receives notification of the wireless connection between the computing device 110 and the electronic medication storage cabinet 104 from the electronic medication storage cabinet 104 (block 710). The server 108 may activate and/or enable the dispensing function for the computing device 110 by updating permissions stored in the server 108, and may transmit instructions for activating and/or enabling the dispensing function on the computing device 110 to the computing device 110 (block 711). The computing device 110 receives the instructions for activating and/or enabling the dispensing function (block 712). Additional details of activating and/or enabling the dispensing function are described above, for example, with reference to FIGS. 1B-1I and 6.

Blocks 713-716 in FIG. 7A show example communications between a computing device 110, an server 108, and an electronic medication storage cabinet 104 for dispensing medications from the electronic medication storage cabinet 104. In response to receiving inputs from a user to dispense one or more ordered medications, such as a clinician's selection of a GUI item associated with dispensing function for the one or more ordered medications, the computing device 110 transmits a request to dispense one or more medications to the server 108 (block 713). The server 108 receives the request to dispense the one or more medications orders (block 714). As described above, the server 108 identifies one or more locations and/or pockets (e.g., identifiers of pockets) in the electronic medication storage cabinet 104 storing the one or more ordered medications indicated in the request. The server 108 transmits instructions to dispense the one or more ordered medications and the identified locations and/or the identifiers of the pockets to the electronic medication storage cabinet 104 (block 715). The electronic medication storage cabinet 104 receives the instructions to dispense the one or more medication orders and the locations and/or the pocket identifiers storing the one or more ordered medications (block 716). Additional details of dispensing medication orders is described above, for example, with reference to FIG. 6.

As described above, in some implementations, a computing device 110 may transmit the request for dispensing medication orders directly to the electronic medication storage cabinet 104 with which a wireless connection is established. Blocks 717-722 show example communications between a computing device 110, an server 108, and an electronic medication storage cabinet 104 for implementations where a computing device 110 transmits a request and/or instruction to dispense medications directly to the electronic medication storage cabinet 104. The computing device 110 transmits a request for the ordered medications directly to the electronic medication storage cabinet 104 (block 717). The electronic medication storage cabinet 104 receives request for dispensing the one or more medication orders (block 718). In response to receiving the request, the electronic medication storage cabinet 104 transmits a request to the server 108 for one or more locations of the medications indicated in the request for dispensing the one or more medication orders (block 719). The server 108 receives requests for locations of the one or more ordered medications (block 720). The server 108 transmits locations of the one or more ordered medications in the electronic medication storage cabinet 104 (block 721) and the electronic medication storage cabinet 104 receives locations of the one or more ordered medications (block 722). The location information may be used by the electronic medication storage cabinet 104 to identify which portion(s) of the cabinet 104 to unlock to provide access to the ordered medication(s). In some implementations, the locations may be provided in a sequence to efficiently unlock and relock areas of the cabinet 104. For example, if two medications are stored in securable pockets within the same drawer, the locations for the two medications may be activated in sequence to avoid having to close, lock, verify, and unlock again the same drawer. In such instances, the system may detect the closure of a first securable pocket and, in response, open the second securable pocket within the same drawer. Additional details of the server 108 of identifying and transmitting locations of the one or more ordered medications in the electronic medication storage cabinets are described above, for example, with reference to FIGS. 1B-1I, 5, and 6.

In some implementations, computing devices 110 may be configured to transmit requests for permissions of one or more functions for a computing device 110 including, but not limited to, one or more medication administration functions associated with locations of the computing devices 110, one or more communication functions (e.g., a passphrase to establish a wireless connection with another computing device), and the like, referred to herein as "location permissions." For example, one or more processors of a computing device 110 may transmit location information of the computing device 110 to the server 108 and a request for location permissions for the computing device 110. As described above, the server 108 may identify one or more location permissions for one or more medication administration functions (e.g., view ordered medications, queue ordered medications, dispense ordered medications, and the like) based on the location information of the computing device 110. Blocks 723-727 show example communications between a computing device 110 and an server 108 for requesting one or more location permissions for the computing device 110. The computing device 110 transmits a request for one or more location permissions to the server 108 (block 723).

The computing device 110 may provide location information of the computing device 110 to the server 108 when transmitting the request for location permissions to the server 108. The server 108 receives request for the one or more location permissions from the computing device 110 (block 724). The server 108 may receive the location information of the computing device 110. The server 108 identifies the location permissions of the computing device 110 (block 725). As described above, the server 108 identifies one or more location permissions based on the location information of the computing device 110. Additional details of identifying the one or more permissions of medication administration functions based on location information of the computing device are described above, for example, with reference to FIGS. 1B-1I and 4. The server 108 transmits the identified location permissions to the computing device 110 (block 726), and the computing device 110 receives the identified location permissions (block 727).

Figure 7C:
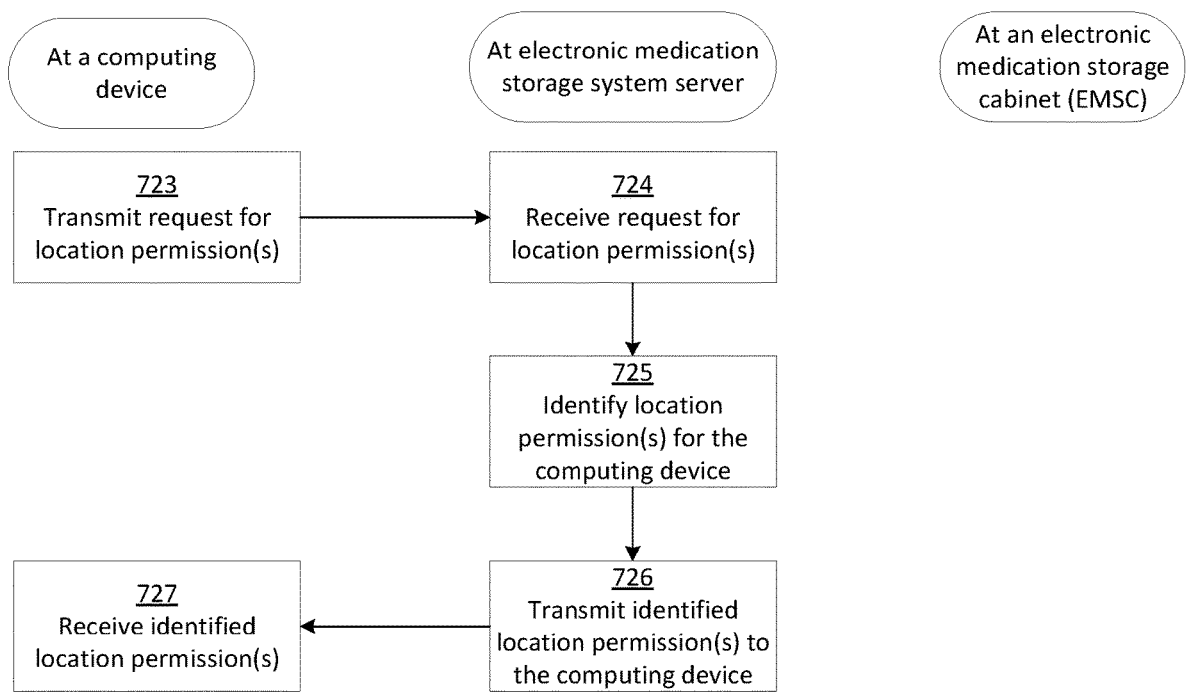

For example, as described above, in some implementations, a computing device 110 may transmit a location permission request to the server 108 for a passphrase to establish a wireless connection with an electronic medication storage cabinet 104, and transmit location information of the computing device 110 to the server 108. The server 108 may determine whether the computing device 110 is within a threshold area and/or distance from the electronic medication storage cabinet 104 based on the location information from received the computing device 110, and transmits the passphrase to the computing device 110 if the server 108 determines that the computing device 110 is within the threshold area and/or the distance. The computing device 110 may initiate and/or establish a wireless connection with the electronic storage cabinet 104 using the passphrase transmitted by the server 108. Example communication flows between the computing device 110, the server 108, and the electronic storage cabinet 104 for initiating and/or establishing wireless connection by the computing device 110 with the electronic storage cabinet 104 that follow block 727 of FIG. 7C are described above, for example, with reference to FIGS. 7A and 7B (e.g., blocks 707-710).

Similarly, the computing device 110 may transmit location information and request location permission for receiving medication orders from the server 108. The server 108 may transmit the medication orders to the computing device 110 if the server 108 determines that the computing device 110 is within a predetermined threshold area and/or distance indicated for receiving medication orders based on the location information transmitted from the computing device 110. Example communication flows between the computing device 110 and the server 108 for the computing device 110 receiving medication orders from the electronic storage cabinet 104 that follow block 727 of FIG. 7C are described above, for example, with reference to FIGS. 7A and 7B (e.g., blocks 701-704), and FIGS. 1B-1C, 5, and 6. In yet another example, the computing device 110 may transmit location information and request location permission for one or more medication administration functionalities, such as viewing, queuing, and/or dispensing medication orders, to the server 108. As described above, based on the received location information, the server 108 may determine whether the computing device 110 is within the one or more threshold areas associated with the functionalities of viewing, queuing, and/or dispensing medication orders, and activate and/or enable the functionalities for the computing device 110. In some implementations, if the server 108 determines that the computing device is not within a predetermined threshold area and/or a predetermined distance associated with a medication administration function for which a location permission is received, then the server 108 may transmit instructions regarding the predetermined threshold area associated with the medication administration function to the computing device 110, to cause a representation of the predetermined threshold area to be displayed on a display device associated with the computing device 110. Example communication flows between the computing device 110, the server 108, and the electronic medication storage cabinet 104, for activating and/or enabling medication administration functionalities, such as viewing, queuing, and/or dispensing medication orders that follow block 727 of FIG. 7C are described above, for example, with reference to FIGS. 7A and 7B (e.g., blocks 705-706, 713-716, 717-722), and FIGS. 1B-1C, 5, and 6.

In some implementations, the electronic medication storage cabinet 104 may be configured to generate an alarm when one or more drawers remain open for a predetermined time period. In some implementations, the electronic medication storage cabinet 104 may be configured to generate an alarm when the computing device 110 with which it is wirelessly connected is not within a threshold proximal distance (e.g., 1.5 feet, 2 feet, and the like) of the electronic medication storage cabinet 104 even if the predetermined time period has not expired. In some implementations, the electronic medication storage cabinet 104 may be configured to not generate an alarm when the computing device 110 within the threshold proximal distance even when the predetermined time period for generating the alarm has expired. In some implementation, the electronic medication storage cabinet 104 may be configured to generate an alarm and transmit a message indicating the one or more open drawers to the computing device 110 that initiated the dispensing process if the computing device 110 is wirelessly connected to the electronic medication storage cabinet 104.

In some implementations, the electronic medication storage cabinet 104 may be configured to transmit a message to the server 108 indicating that one or more drawers and/or pockets of the electronic medication storage cabinet 104 are open. The server 108 may determine whether location of the computing device 110 that is wirelessly connected to the electronic medication storage cabinet 104 is within a threshold distance from the electronic medication storage cabinet 104 (e.g., proximal to the electronic medication storage cabinet 104, 1 feet from the electronic medication storage cabinet 104, and the like). If the server 108 determines that the location of the computing device 110 is within the threshold distance from the electronic medication storage cabinet 104, then the server 108 may cause an alarm of the electronic medication storage cabinet 104 to be suspended, where the alarm may be configured to be triggered when a drawer and/or a pocket the electronic medication storage cabinet 104 remains open for the above described predetermined time period and/or longer.

For example, the server 108 may transmit an instruction to the electronic medication storage cabinet 104 to suspend the corresponding alarm. If the server 108 determines that the location of the computing device 110 is not within the threshold distance from the electronic medication storage cabinet 104, then the server 108 may cause the corresponding alarm of the electronic medication storage cabinet 104 to be activated. In some implementation, if the computing device 110 is no longer wirelessly connected to the electronic medication storage cabinet 104, then the electronic medication storage cabinet 104 may transmit a message to the server 108 to transmit a message to the computing device 110 that initiated the most recent dispensing process that one or more open drawers of the electronic medication storage cabinet 104 are open.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software, or any combination thereof.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of the Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method, comprising: receiving a current location of a computing device; determining, based on the current location of the computing device, whether the computing device is within a first predetermined area associated with predetermined medication administration functions that, when activated, operate one or more electronic medication storage cabinets; confirming a user of the computing device is authorized to receive information pertaining to one or more medications associated with one or more patients; providing, for display at the computing device, based on confirming the user is authorized, a graphical user interface including respective representations of one or more first medication administration functions and one or more second medication administration functions associated with storage of the one or more medications; in response to determining that the computing device is within the first predetermined area: enabling the computing device to perform the one or more first medication administration functions associated with the first predetermined area to cause, responsive to a selection of a displayed representation of the one or more first medication administration functions, a respective electronic medication storage cabinet associated with the selected displayed representation to perform an operation regarding a physical storage of a medication associated with a patient of the one or more patients; and preventing the computing device from performing the one or more second medication administration functions not associated with the first predetermined area, wherein the respective electronic medication storage cabinet is remote from the computing device.

Clause 2. The method of Clause 1, wherein the one or more enabled medication administration functions includes queuing medications, the method further comprising: receiving, from the computing device, a request to queue one or more medications to dispense for the patient; identifying, based on the request and a stored mapping between the one or more medications and the one or more electronic medication storage cabinets, a first electronic medication storage cabinet storing the one or more medications; and causing representations of at least one medication administration function of the first electronic medication storage cabinet to be enabled or disabled in the graphical interface according to the first predetermined area in which the computing device is located and a prior association between the at least one medication administration function and the first electronic medication storage cabinet.

Clause 3. The method of Clause 2, further comprising: identifying a plurality of electronic medication storage cabinets associated with the first predetermined area; identifying a second electronic medication storage cabinet of the plurality of electronic medication storage cabinets as an optimal electronic medication storage cabinet based on a location of the second electronic medication storage cabinet and an amount of medications prescribed for the patient that are stored in the second electronic medication storage cabinet; causing the graphical interface to display identifiers for the plurality of electronic medication storage cabinets associated with the first predetermined area; and causing a graphical indication to be displayed proximal to the identifier of the optimal electronic medication storage cabinet on the display device associated with the computing device.

Clause 4. The method of Clause 1, wherein one of the one or more enabled medication administration functions is queuing medications and the method further comprising: causing the graphical user interface to display respective identifiers for the one or more electronic medication storage cabinets; receiving, based on the display of the respective identifiers, a selection of an electronic medication storage cabinet to which to queue one or more medications; determining, based on the location information of the computing device, whether the computing device is within a first threshold distance from the selected electronic medication storage cabinet; and in response to determining that the computing device is within the first threshold distance, transmitting a passphrase to the computing device to cause the computing device to establish a wireless connection with the electronic medication storage cabinet.

Clause 5. The method of Clause 4, further comprising: receiving, from the electronic medication storage cabinet, a message indicating a successful wireless connection with the computing device; in response to receiving the message, enabling, for the computing device, a medication administration function of dispensing medication; and causing the graphical user interface to display the medication dispensing function as enabled.

Clause 6. The method of Clause 5, further comprising: receiving a request for dispensing a set of medications from the electronic medication storage cabinet; identifying, based a stored mapping between identifiers of the set of medications and pockets of the electronic medication storage cabinet, one or more pockets storing the set of medications; and transmitting an instruction to dispense medication from the identified one or more pockets to the electronic medication storage cabinet.

Clause 7. The method of Clause 6, further comprising: automatically determining when the computing device is within a second threshold distance of the selected electronic medication storage cabinet; and causing, when the computing device is within the second threshold distance of the electronic medication storage cabinet, a first drawer of the electronic medication storage cabinet to open, wherein the first drawer comprises a first pocket of the one or more identified pockets.

Clause 8. The method of Clause 5, further comprising: receiving, from the electronic medication storage cabinet, a request for locations within the electronic medication storage cabinet for a set of medications in a dispensing request received by the electronic medication storage cabinet; in response to the request for locations, identifying, based on a mapping between medications and pockets of the electronic medication storage cabinet and the set of medications, one or more pockets of the electronic medication storage cabinet; and transmitting the one or more pockets along with corresponding medications to the electronic medication storage cabinet.

Clause 9. The method of Clause 8, further comprising: receiving, from the electronic medication storage cabinet, a message indicating one or more drawers of the electronic medication storage cabinet are open; determining, based on the location information of the computing device, whether the computing device is within a threshold distance from the electronic medication storage cabinet; and in response to determining the computing device is within the threshold distance, suspending an alarm of the electronic medication storage cabinet configured to indicate that the one or more drawers are open for a predetermined period of time.

Clause 10. The method of Clause 1, further comprising: receiving a request for permission to enable a medication administration function of the one or more second medication administration functions not associated with the first predetermined area; and providing, responsive to the request, for display at the computing device, a representation of the predetermined area associated with the medication administration function.

Clause 11. A system comprising: a memory storing instructions; and one or more processors coupled with the memory and configured to execute the instructions to cause the system to: receive a current location of a computing device; determine, based on the current location of the computing device, whether the computing device is within a first predetermined area associated with predetermined medication administration functions that, when activated, operate one or more electronic medication storage cabinets; confirm a user of the computing device is authorized to receive information pertaining to one or more medications associated with one or more patients; provide, for display at the computing device, based on confirming the user is authorized, a graphical user interface including respective representations of one or more first medication administration functions and one or more second medication administration functions associated with storage of the one or more medications; and when the computing device is within the first predetermined area: enable the computing device to perform one or more first medication administration functions associated with the first predetermined area to cause, responsive to a selection of a displayed representation of the one or more first medication administration functions, a respective electronic medication storage cabinet associated with the selected displayed representation to perform an operation regarding a physical storage of a medication associated with a patient of the one or more patients; and prevent the computing device from performing one or more second medication administration functions not associated with the first predetermined area, wherein the respective electronic medication storage cabinet is remote from the computing device.

Clause 12. The system of Clause 11, wherein the one or more processors are configured to execute instructions to cause the system to: receive, from the computing device, a request to queue one or more medications to dispense for the patient; identify, based on the request and a stored mapping between the one or more medications and the one or more electronic medication storage cabinets, a first electronic medication storage cabinet storing the one or more medications; and cause representations of at least one medication administration function of the first electronic medication storage cabinet to be enabled or disabled in the graphical interface according to the first predetermined area in which the computing device is located and a prior association between the at least one medication administration function and the first electronic medication storage cabinet.

Clause 13. The system of Clause 12, wherein the one or more processors are configured to execute instructions to cause the system to: identify a plurality of electronic medication storage cabinets associated with the first predetermined area; identify a second electronic medication storage cabinet of the plurality of electronic medication storage cabinets as an optimal electronic medication storage cabinet based on a location of the second electronic medication storage cabinet and an amount of medications prescribed for the patient that are stored in the second electronic medication storage cabinet; cause the graphical interface to display identifiers for the plurality of electronic medication storage cabinets associated with the first predetermined area; and cause a graphical indication to be displayed proximal to the identifier of the optimal electronic medication storage cabinet on the display device associated with the computing device.

Clause 14. The system of Clause 11, wherein the one or more processors are configured to execute instructions to cause the system to: cause the graphical user interface to display respective identifiers for the one or more electronic medication storage cabinets; receive, based on the display of the respective identifiers, a selection of an electronic medication storage cabinet to which to queue one or more medications; determine, based on the location information of the computing device, whether the computing device is within a first threshold distance from the selected electronic medication storage cabinet; and when the computing device is within the first threshold distance, transmit a passphrase to the computing device to cause the computing device to establish a wireless connection with the electronic medication storage cabinet.

Clause 15. The system of Clause 14, wherein the one or more processors are configured to execute instructions to cause the system to: receive, from the electronic medication storage cabinet, a message indicating a successful wireless connection with the computing device; when the message, enabling, for the computing device, a medication administration function of dispensing medication; and cause the graphical user interface to display the medication dispensing function as enabled.

Clause 16. The system of Clause 15, wherein the one or more processors are configured to execute instructions to cause the system to: receive a request for dispensing a set of medications from the electronic medication storage cabinet; identify, based a stored mapping between identifiers of the set of medications and pockets of the electronic medication storage cabinet, one or more pockets storing the set of medications; and transmit an instruction to dispense medication from the identified one or more pockets to the electronic medication storage cabinet.

Clause 17. The system of Clause 16, wherein the one or more processors are configured to execute instructions to cause the system to: automatically determine when the computing device is within a second threshold distance of the selected electronic medication storage cabinet; and cause, when the computing device is within the second threshold distance of the electronic medication storage cabinet, a first drawer of the electronic medication storage cabinet to open, wherein the first drawer comprises a first pocket of the one or more identified pockets.

Clause 18. The system of Clause 15, wherein the one or more processors are configured to execute instructions to cause the system to: receive, from the electronic medication storage cabinet, a request for locations within the electronic medication storage cabinet for a set of medications in a dispensing request received by the electronic medication storage cabinet; in response to the request for locations, identify, based on a mapping between medications and pockets of the electronic medication storage cabinet and the set of medications, one or more pockets of the electronic medication storage cabinet; and transmit the one or more pockets along with corresponding medications to the electronic medication storage cabinet.

Clause 19. The system of Clause 18, wherein the one or more processors are configured to execute instructions to cause the system to: receive, from the electronic medication storage cabinet, a message indicating one or more drawers of the electronic medication storage cabinet are open; determine, based on the location information of the computing device, whether the computing device is within a threshold distance from the electronic medication storage cabinet; and when the computing device is within the threshold distance, suspending an alarm of the electronic medication storage cabinet configured to indicate that the one or more drawers are open for a predetermined period of time.

Clause 20. The system of Clause 11, wherein the one or more processors are configured to execute instructions to cause the system to: receive a request for permission to enable a medication administration function of the one or more second medication administration functions not associated with the first predetermined area; and providing, responsive to the request, for display at the computing device, a representation of the predetermined area associated with the medication administration function.

Clause 21. A non-transitory computer-readable medium storing instructions thereon that, when executed by a computing device, perform a method comprising: receiving a current location of a computing device; determining, based on the current location of the computing device, whether the computing device is within a first predetermined area associated with predetermined medication administration functions that, when activated, operate one or more electronic medication storage cabinets; confirming a user of the computing device is authorized to receive information pertaining to one or more medications associated with one or more patients; providing, for display at the computing device, based on confirming the user is authorized, a graphical user interface including respective representations of one or more first medication administration functions and one or more second medication administration functions associated with storage of the one or more medications; in response to determining that the computing device is within the first predetermined area: enabling the computing device to perform the one or more first medication administration functions associated with the first predetermined area to cause, responsive to a selection of a displayed representation of the one or more first medication administration functions, a respective electronic medication storage cabinet associated with the selected displayed representation to perform an operation regarding a physical storage of a medication associated with a patient of the one or more patients; and preventing the computing device from performing the one or more second medication administration functions not associated with the first predetermined area, wherein the respective electronic medication storage cabinet is remote from the computing device.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A method, comprising:
receiving a current location of a mobile computing device from a global positioning system (GPS) of a computing device;
confirming a user of the mobile computing device is authorized to receive information pertaining to one or more medications associated with one or more patients;
providing, for display at the mobile computing device, based on confirming the user is authorized, a graphical user interface including representations of a plurality of medication administration functions associated with the one or more patients;
based on the current location of the mobile computing device:
causing the user interface to enable a display of one or more first functions of the medication administration functions for selection when the received current location is a first predetermined area; and
causing the user interface to disable the display of the one or more first functions and to enable a display of one or more second functions of the medication administration functions for selection when the received current location is a second predetermined area,
wherein each of the first and second functions is configured to, when displayed and selected from the user interface by the user, remotely cause a respective electronic medication storage cabinet associated with the selected function to perform an operation regarding a physical storage of a medication associated with a patient of the one or more patients;
determining, based on the received current location of the mobile computing device, whether the mobile computing device is within a first threshold distance from a selected electronic medication storage cabinet;
in response to determining that the mobile computing device is within the first threshold distance:
transmitting a credential to the mobile computing device to cause the mobile computing device to establish a short range wireless connection with the electronic medication storage cabinet, and
causing the graphical user interface to display a medication administration function for dispense of medication from the selected electronic medication storage cabinet as being enabled based on the short range wireless connection being established;
receiving, while the mobile computing device is within a first threshold distance from the selected electronic medication storage cabinet, an indication the enabled medication administration function was selected and a request to dispense a selected medication for the patient; and transmitting, responsive to the request, an instruction to cause dispense of the selected medication from the electronic medication storage cabinet.

2. The method of claim 1, further comprising:
enabling one or more medication administration functions based on the current location, wherein the one or more enabled medication administration functions includes queuing medications, the method further comprising:
receiving, from the mobile computing device, a request to queue one or more medications to dispense for a patient;
identifying, based on the request to queue the one or more medications, a first electronic medication storage cabinet storing the one or more medications; and
causing representations of at least one medication administration function of the first electronic medication storage cabinet to be enabled or disabled in the graphical user interface according to the first predetermined area in which the mobile computing device is located and a prior association between the at least one medication administration function and the first electronic medication storage cabinet.

3. The method of claim 2, further comprising:
identifying a plurality of electronic medication storage cabinets associated with the first predetermined area;
identifying a second electronic medication storage cabinet of the plurality of electronic medication storage cabinets as an optimal electronic medication storage cabinet based on a location of the second electronic medication storage cabinet and an amount of medications prescribed for the patient that are stored in the second electronic medication storage cabinet;
causing the graphical user interface to display identifiers for the plurality of electronic medication storage cabinets associated with the first predetermined area; and
causing a graphical indication to be displayed proximal to the identifier of the optimal electronic medication storage cabinet on a display device associated with the mobile computing device.

4. The method of claim 1, wherein one of the one or more enabled medication administration functions is queuing medications and the method further comprising:
causing the graphical user interface to display respective identifiers for one or more electronic medication storage cabinets;
receiving, based on the display of the respective identifiers, a selection of the selected electronic medication storage cabinet to which to queue one or more medications.

5. The method of claim 4, further comprising:
receiving, from the electronic medication storage cabinet, a message indicating a successful wireless connection with the mobile computing device;
in response to receiving the message, enabling, for the mobile computing device, a medication administration function for dispense of the medication.

6. The method of claim 5, further comprising:
identifying, based a stored mapping between identifiers of the selected medication and pockets of the electronic medication storage cabinet, one or more pockets storing the selected medication,
wherein transmitting the instruction to dispense the medication comprises causing the dispense of the selected medication from the identified one or more pockets.

7. The method of claim 6, further comprising:
automatically determining when the mobile computing device is within a second threshold distance of the selected electronic medication storage cabinet; and
causing, when the mobile computing device is within the second threshold distance of the electronic medication storage cabinet, a first drawer of the electronic medication storage cabinet to open, wherein the first drawer comprises a first pocket of the one or more identified pockets.

8. The method of claim 5, further comprising:
receiving, from the electronic medication storage cabinet, a request for locations within the electronic medication storage cabinet for a selected medication in a dispensing request received by the electronic medication storage cabinet;
in response to the request for locations, identifying, based on a mapping between medications and pockets of the electronic medication storage cabinet and the selected medication, one or more pockets of the electronic medication storage cabinet; and
transmitting respective locations of the identified one or more pockets medications.

9. The method of claim 8, further comprising:
receiving, from the electronic medication storage cabinet, a message indicating one or more drawers of the electronic medication storage cabinet are open;
determining, based on the received current location of the mobile computing device, whether the mobile computing device is within a second threshold distance from the electronic medication storage cabinet; and
in response to determining the mobile computing device is within the second threshold distance, suspending an alarm of the electronic medication storage cabinet configured to indicate that the one or more drawers are open for a predetermined period of time.

10. The method of claim 1, further comprising:
receiving a request for permission to enable a medication administration function of one or more second medication administration functions not associated with the first predetermined area; and
providing, responsive to the request, for display at the mobile computing device, a representation of the predetermined area associated with the medication administration function.

11. A system comprising:
a memory storing instructions; and
one or more processors coupled with the memory and configured to execute the instructions to cause the system to:
receive a current location of a mobile computing device from a global positioning system of the computing device;
confirm a user of the mobile computing device is authorized to receive information pertaining to one or more medications associated with one or more patients;
provide, for display at the mobile computing device, based on confirming the user is authorized, a graphical user interface representations of a plurality of medication administration functions associated with the one or more patients; and
based on the current location of the mobile computing device:
cause the user interface to enable a display of one or more first functions of the medication administration functions for selection when the received current location is a first predetermined area;

cause the user interface to disable the display of the one or more first functions and to enable a display of one or more second functions of the medication administration functions for selection when the received current location is a second predetermined area, wherein each of the first and second functions is configured to, when displayed and selected from the user interface by the user, remotely cause a respective electronic medication storage cabinet associated with the selected function to perform an operation regarding a physical storage of a medication associated with a patient of the one or more patients; and determine, based on the received current location of the mobile computing device, whether the mobile computing device is within a first threshold distance from a selected electronic medication storage cabinet;

in response to determining that the mobile computing device is within the first threshold distance:

transmit a credential to the mobile computing device to cause the mobile computing device to establish a short range wireless connection with the electronic medication storage cabinet, and cause the graphical user interface to display a medication administration function for dispense of medication from the selected electronic medication storage cabinet as being enabled based on the short range wireless connection being established;

receive, while the mobile computing device is within a first threshold distance from the selected electronic medication storage cabinet, an indication the enabled medication administration function was selected and a request to dispense a selected medication for the patient; and transmit, responsive to the request, an instruction to cause dispense of the selected medication from the electronic medication storage cabinet.

12. The system of claim 11, wherein the one or more processors are configured to execute instructions to cause the system to:

receive, from the mobile computing device, a request to queue one or more medications to dispense for a patient;

identify, based on the request to queue the one or more medications, a first electronic medication storage cabinet storing the one or more medications; and cause representations of at least one medication administration function of the first electronic medication storage cabinet to be enabled or disabled in the graphical user interface according to the first predetermined area in which the mobile computing device is located and a prior association between the at least one medication administration function and the first electronic medication storage cabinet.

13. The system of claim 12, wherein the one or more processors are configured to execute instructions to cause the system to:

identify a plurality of electronic medication storage cabinets associated with the first predetermined area;

identify a second electronic medication storage cabinet of the plurality of electronic medication storage cabinets as an optimal electronic medication storage cabinet based on a location of the second electronic medication storage cabinet and an amount of medications prescribed for the patient that are stored in the second electronic medication storage cabinet;

cause the graphical user interface to display identifiers for the plurality of electronic medication storage cabinets associated with the first predetermined area; and cause a graphical indication to be displayed proximal to the identifier of the optimal electronic medication storage cabinet on a display device associated with the mobile computing device.

14. The system of claim 11, wherein the one or more processors are configured to execute instructions to cause the system to:

cause the graphical user interface to display respective identifiers for one or more electronic medication storage cabinets; and receive, based on the display of the respective identifiers, a selection of the selected electronic medication storage cabinet to which to queue one or more medications.

15. The system of claim 14, wherein the one or more processors are configured to execute instructions to cause the system to:

receive, from the electronic medication storage cabinet, a message indicating a successful wireless connection with the mobile computing device; and when the message is received, enabling, for the mobile computing device, a medication administration function of dispensing medication.

16. The system of claim 15, wherein the one or more processors are configured to execute instructions to cause the system to:

identify, based a stored mapping between identifiers of the selected medication and pockets of the electronic medication storage cabinet, one or more pockets storing the selected medication, wherein transmitting the instruction to dispense the selected medication comprises causing the dispense of the selected medication from the identified one or more pockets to the electronic medication storage cabinet.

17. The system of claim 16, wherein the one or more processors are configured to execute instructions to cause the system to:

automatically determine when the mobile computing device is within a second threshold distance of the selected electronic medication storage cabinet; and cause, when the mobile computing device is within the second threshold distance of the electronic medication storage cabinet, a first drawer of the electronic medication storage cabinet to open, wherein the first drawer comprises a first pocket of the one or more identified pockets.

18. The system of claim 15, wherein the one or more processors are configured to execute instructions to cause the system to:

receive, from the electronic medication storage cabinet, a request for locations within the electronic medication storage cabinet for a selected medication in a dispensing request received by the electronic medication storage cabinet;

in response to the request for locations, identify, based on a mapping between medications and pockets of the electronic medication storage cabinet and the selected medication, one or more pockets of the electronic medication storage cabinet; and transmit respective locations of the identified one or more pockets.

19. The system of claim 18, wherein the one or more processors are configured to execute instructions to cause the system to:

receive, from the electronic medication storage cabinet, a message indicating one or more drawers of the electronic medication storage cabinet are open;

determine, based on the received current location of the mobile computing device, whether the mobile computing device is within a second threshold distance from the electronic medication storage cabinet; and when the mobile computing device is within the second threshold distance, suspending an alarm of the electronic medication storage cabinet configured to indicate that the one or more drawers are open for a predetermined period of time.

20. The system of claim 11, wherein the one or more processors are configured to execute instructions to cause the system to:

receive a request for permission to enable a medication administration function of the one or more second medication administration functions not associated with the first predetermined area; and providing, responsive to the request, for display at the mobile computing device, a representation of the predetermined area associated with the medication administration function.

21. A non-transitory computer-readable medium storing instructions thereon that, when executed by a mobile computing device, perform a method comprising:

receiving a current location of a mobile computing device from a global positioning system (GPS) of a mobile computing device;

confirming a user of the mobile computing device is authorized to receive information pertaining to one or more medications associated with one or more patients;

providing, for display at the mobile computing device, based on confirming the user is authorized, a graphical user interface including representations of a plurality of medication administration functions associated with the one or more patients;

based on the current location of the mobile computing device:

causing the user interface to enable a display of one or more first functions of the medication administration functions for selection when the received current location is a first predetermined area; and causing the user interface to disable the display of the one or more first functions and to enable a display of one or more second functions of the medication administration functions for selection when the received current location is a second predetermined area, wherein each of the first and second functions is configured to, when displayed and selected from the user interface by the user, remotely cause a respective electronic medication storage cabinet associated with the selected function to perform an operation regarding a physical storage of a medication associated with a patient of the one or more patients; and determining, based on the received current location of the mobile computing device, whether the mobile computing device is within a first threshold distance from a selected electronic medication storage cabinet;

in response to determining that the mobile computing device is within the first threshold distance:

transmitting a credential to the mobile computing device to cause the mobile computing device to establish a short range wireless connection with the electronic medication storage cabinet, and causing the graphical user interface to display a medication administration function for dispense of medication from the selected electronic medication storage cabinet as being enabled based on the short range wireless connection being established;

receiving, while the mobile computing device is within a first threshold distance from the selected electronic medication storage cabinet, an indication the enabled medication administration function was selected and a request to dispense a selected medication for the patient; and transmitting, responsive to the request, an instruction to cause dispense of the selected medication from the electronic medication storage cabinet.

* * * * *